(12) United States Patent
Gamroth et al.

(10) Patent No.: US 11,274,842 B2
(45) Date of Patent: Mar. 15, 2022

(54) SYSTEMS AND METHODS FOR OPTIMIZING VENTILATION, FILTRATION, AND CONDITIONING SCHEMES FOR BUILDINGS

(71) Applicant: Johnson Controls Technology Company, Auburn Hills, MI (US)

(72) Inventors: Timothy C. Gamroth, Dousman, WI (US); Michael J. Wenzel, Grafton, WI (US); Mohammad N. ElBsat, Milwaukee, WI (US); David S. Eidson, Franklin, WI (US); James Burke, Milwaukee, WI (US); Kirk H. Drees, Cedarburg, WI (US); Thomas M. Seneczko, Milwaukee, WI (US)

(73) Assignee: Johnson Controls Tyco IP Holdings LLP, Milwaukee, WI (US)

( * ) Notice: Subject to any disclaimer, the term of this patent is extended or adjusted under 35 U.S.C. 154(b) by 0 days.

(21) Appl. No.: 16/927,063

(22) Filed: Jul. 13, 2020

(65) Prior Publication Data
US 2021/0010693 A1 Jan. 14, 2021

Related U.S. Application Data

(60) Provisional application No. 62/873,631, filed on Jul. 12, 2019, provisional application No. 63/044,906, (Continued)

(51) Int. Cl.
*F24F 11/00* (2018.01)
*F24F 8/10* (2021.01)
(Continued)

(52) U.S. Cl.
CPC ............ *F24F 11/0001* (2013.01); *F24F 3/14* (2013.01); *F24F 8/10* (2021.01); *F24F 11/39* (2018.01);
(Continued)

(58) Field of Classification Search
None
See application file for complete search history.

(56) References Cited

U.S. PATENT DOCUMENTS

| 6,988,671 B2 | 1/2006 | Deluca |
| 7,025,281 B2 | 4/2006 | Deluca |
| | (Continued) | |

FOREIGN PATENT DOCUMENTS

| CN | 101387428 A | 3/2009 |
| CN | 107477782 A | 12/2017 |
| | (Continued) | |

OTHER PUBLICATIONS

Aghniaey et al., "The Assumption of Equidistance in the Seven-Point Thermal Sensation Scale and a Comparison between Categorical and Continuous Metrics," University of Georgia College of Engineering, Jan. 18, 2019, 4 pages.
(Continued)

*Primary Examiner* — Kenneth M Lo
*Assistant Examiner* — Istiaque Ahmed
(74) *Attorney, Agent, or Firm* — Foley & Lardner LLP

(57) ABSTRACT

A building management system (BMS) for filtering a fluid within a building is shown. The system includes one or more sensors configured to measure one or more characteristics of a first fluid within an air duct of the BMS and measure one or more characteristics of a second fluid after the second fluid has been filtered. The system further includes a pollutant management system configured to receive data from the one or more sensors and control a filtration process. The filtration process selects a filter of a plurality of filters based on a level of the one or more characteristics of the first fluid and the one or more characteristics of the second fluid.

20 Claims, 12 Drawing Sheets

Related U.S. Application Data filed on Jun. 26, 2020, provisional application No. 63/046,376, filed on Jun. 30, 2020, provisional application No. 63/047,119, filed on Jul. 1, 2020.

(51) Int. Cl.

| | | |
|---|---|---|
| *F24F 11/64* | (2018.01) | |
| *F24F 11/46* | (2018.01) | |
| *F24F 11/72* | (2018.01) | |
| *F24F 3/14* | (2006.01) | |
| *G16H 40/20* | (2018.01) | |
| *G16H 50/30* | (2018.01) | |
| *G05B 19/042* | (2006.01) | |
| *F24F 11/39* | (2018.01) | |
| *F24F 11/61* | (2018.01) | |
| *G05B 13/04* | (2006.01) | |
| *F24F 120/10* | (2018.01) | |
| *F24F 140/60* | (2018.01) | |
| *F24F 120/20* | (2018.01) | |
| *F24F 110/65* | (2018.01) | |
| *F24F 8/22* | (2021.01) | |
| *F24F 110/64* | (2018.01) | |
| *F24F 110/70* | (2018.01) | |
| *F24F 110/74* | (2018.01) | |

(52) U.S. Cl.
CPC .............. *F24F 11/46* (2018.01); *F24F 11/61* (2018.01); *F24F 11/64* (2018.01); *F24F 11/72* (2018.01); *G05B 13/041* (2013.01); *G05B 19/042* (2013.01); *G16H 40/20* (2018.01); *G16H 50/30* (2018.01); *F24F 8/22* (2021.01); *F24F 2110/64* (2018.01); *F24F 2110/65* (2018.01); *F24F 2110/70* (2018.01); *F24F 2110/74* (2018.01); *F24F 2120/10* (2018.01); *F24F 2120/20* (2018.01); *F24F 2140/60* (2018.01); *G05B 2219/25011* (2013.01); *G05B 2219/2614* (2013.01)

(56) References Cited

U.S. PATENT DOCUMENTS

| | | | |
|---|---|---|---|
| 7,099,895 | B2 | 8/2006 | Dempsey |
| 7,150,408 | B2 | 12/2006 | Deluca |
| 7,222,494 | B2 | 5/2007 | Peterson et al. |
| 7,311,752 | B2 | 12/2007 | Tepper et al. |
| 7,394,370 | B2 | 7/2008 | Chan |
| 7,817,046 | B2 | 10/2010 | Coveley et al. |
| 7,941,096 | B2 | 5/2011 | Perkins et al. |
| 8,049,614 | B2 | 11/2011 | Kahn et al. |
| 8,405,503 | B2 | 3/2013 | Wong |
| 8,862,448 | B2 | 10/2014 | Holmes et al. |
| 8,867,993 | B1 | 10/2014 | Perkins et al. |
| 8,984,464 | B1 | 3/2015 | Mihal et al. |
| 9,075,909 | B2 | 7/2015 | Almogy et al. |
| 9,465,392 | B2 | 10/2016 | Bradley et al. |
| 9,618,224 | B2 | 4/2017 | Emmons et al. |
| 9,741,233 | B2 | 8/2017 | Laufer et al. |
| 9,810,441 | B2 | 11/2017 | Dean-Hendricks et al. |
| 9,915,438 | B2 | 3/2018 | Cheatham et al. |
| 10,068,116 | B2 | 9/2018 | Good et al. |
| 10,198,779 | B2 | 2/2019 | Pittman et al. |
| 10,251,610 | B2 | 4/2019 | Parthasarathy et al. |
| 10,359,748 | B2 | 7/2019 | Elbsat et al. |
| 10,528,020 | B2 | 1/2020 | Drees |
| 10,706,375 | B2 | 7/2020 | Wenzel et al. |
| 2007/0101688 | A1* | 5/2007 | Wootton ............ B01D 46/0036 55/385.2 |
| 2007/0202798 | A1 | 8/2007 | Billiotte et al. |
| 2007/0219645 | A1 | 9/2007 | Thomas et al. |
| 2008/0206767 | A1 | 8/2008 | Kreiswirth et al. |
| 2009/0078120 | A1 | 3/2009 | Kummer et al. |
| 2009/0117798 | A1 | 5/2009 | Takashima et al. |
| 2009/0126382 | A1 | 5/2009 | Rubino et al. |
| 2010/0047115 | A1 | 2/2010 | Krichtafovitch et al. |
| 2010/0175556 | A1 | 7/2010 | Kummer et al. |
| 2010/0198611 | A1 | 8/2010 | Ruoff et al. |
| 2011/0093249 | A1 | 4/2011 | Holmes et al. |
| 2011/0172981 | A1 | 7/2011 | Al-Hashimi et al. |
| 2012/0112883 | A1 | 5/2012 | Wallace et al. |
| 2012/0130547 | A1 | 5/2012 | Fadell et al. |
| 2012/0199003 | A1 | 8/2012 | Melikov et al. |
| 2014/0167917 | A2 | 6/2014 | Wallace et al. |
| 2014/0260692 | A1* | 9/2014 | Sharp ................... G01N 1/2273 73/863.23 |
| 2014/0283682 | A1* | 9/2014 | Hamann ............. B01D 46/442 95/10 |
| 2015/0028114 | A1 | 1/2015 | Rosen |
| 2015/0053366 | A1 | 2/2015 | Melsheimer |
| 2015/0097688 | A1 | 4/2015 | Bruck et al. |
| 2015/0109442 | A1 | 4/2015 | Derenne et al. |
| 2015/0316907 | A1 | 11/2015 | Elbsat et al. |
| 2015/0354874 | A1* | 12/2015 | Cur ......................... F24F 13/28 62/216 |
| 2016/0066068 | A1 | 3/2016 | Schultz et al. |
| 2016/0109149 | A1 | 4/2016 | Heller |
| 2016/0116181 | A1 | 4/2016 | Aultman et al. |
| 2016/0210337 | A1 | 7/2016 | Constandt |
| 2016/0306934 | A1 | 10/2016 | Sperry et al. |
| 2016/0377306 | A1 | 12/2016 | Drees et al. |
| 2017/0016644 | A1 | 1/2017 | Nagarathinam et al. |
| 2017/0039339 | A1 | 2/2017 | Bitran et al. |
| 2017/0097163 | A1 | 4/2017 | Law et al. |
| 2017/0123440 | A1 | 5/2017 | Mangsuli et al. |
| 2017/0147722 | A1 | 5/2017 | Greenwood |
| 2017/0193792 | A1 | 7/2017 | Rodriguez et al. |
| 2017/0206334 | A1 | 7/2017 | Huang |
| 2017/0211837 | A1 | 7/2017 | Gupta et al. |
| 2017/0246331 | A1 | 8/2017 | Lloyd |
| 2017/0350611 | A1* | 12/2017 | Su ............................ F24F 11/30 |
| 2017/0351832 | A1 | 12/2017 | Cahan et al. |
| 2018/0052970 | A1 | 2/2018 | Boss et al. |
| 2018/0087791 | A1 | 3/2018 | Monkkonen et al. |
| 2018/0110416 | A1 | 4/2018 | Masuda et al. |
| 2018/0117209 | A1 | 5/2018 | Clack et al. |
| 2018/0204162 | A1 | 7/2018 | Endel et al. |
| 2018/0285800 | A1 | 10/2018 | Wenzel et al. |
| 2018/0318746 | A1 | 11/2018 | Thomas |
| 2018/0357577 | A1 | 12/2018 | Elbsat et al. |
| 2019/0096233 | A1 | 3/2019 | Bruck et al. |
| 2019/0108746 | A1 | 4/2019 | Chang et al. |
| 2019/0209806 | A1 | 7/2019 | Allen et al. |
| 2019/0219293 | A1 | 7/2019 | Wenzel et al. |
| 2019/0249897 | A1 | 8/2019 | Perez et al. |
| 2019/0331358 | A1 | 10/2019 | Ritmanich et al. |
| 2019/0347622 | A1 | 11/2019 | Elbsat et al. |
| 2020/0090089 | A1 | 3/2020 | Aston et al. |
| 2020/0125045 | A1 | 4/2020 | Risdeck et al. |
| 2020/0141734 | A1 | 5/2020 | Casarez et al. |
| 2020/0176124 | A1 | 6/2020 | Chatterjea et al. |
| 2020/0176125 | A1 | 6/2020 | Chatterjea et al. |
| 2020/0227159 | A1 | 7/2020 | Boisvert et al. |
| 2020/0348038 | A1 | 11/2020 | Risdeck et al. |
| 2021/0043330 | A1 | 2/2021 | Ikeshima |

FOREIGN PATENT DOCUMENTS

| | | |
|---|---|---|
| CN | 108980988 A | 12/2018 |
| CN | 109405151 A | 3/2019 |
| CN | 110529988 A | 12/2019 |
| CN | 110671798 A | 1/2020 |
| CN | 110822616 A | 2/2020 |
| FR | 3031800 A1 | 7/2016 |
| JP | 2010-128976 A | 6/2010 |
| JP | 2012-533720 A | 12/2012 |
| JP | 2015-152175 A | 8/2015 |
| JP | 2016-138705 A | 8/2016 |
| JP | 06-455326 B2 | 1/2019 |
| KR | 20160137767 A | 12/2016 |
| KR | 20170115913 A | 10/2017 |

(56) References Cited

FOREIGN PATENT DOCUMENTS

| KR | 101865143 B1 | 6/2018 |
|---|---|---|
| KR | 20200047457 A | 5/2020 |
| WO | WO-2016/047103 A1 | 3/2016 |
| WO | WO-2017/203031 A1 | 11/2017 |
| WO | WO-2019/051893 A1 | 3/2019 |
| WO | WO-2019/157514 A2 | 8/2019 |

OTHER PUBLICATIONS

Batterman et al., "Review and Extension of CO2-Based Methods to Determine Ventilation Rates with Application to School Classrooms," International Journal of Environmental Research and Public Health, Feb. 4, 22 pages.

Chen et al., "Occupant Feedback Based Model Predictive Control for Thermal Comfort and Energy Optimization: A Chamber Experimental Evaluation," Applied Energy, 2016, 164, pp. 341-351.

HVAC Filtration and the Wells-Riley Approach to Assessing Risks of Infectious Airborne Diseases (Year: 2012).

Kang et al., "Novel Modeling and Control Strategies for a HVAC System Including Carbon Dioxide Control," Energies, Jun. 2, 2014, 7, pp. 3599-3617.

Lampinen, "Thermodynamics of Humid Air," Sep. 2015, 39 Pages.

Ljung, System Identification: Theory for the User, 1999, 2nd ed., Prentice Hall PTR, Upper Saddle River, 63 pages.

Luo, "Maximizing Thermal Comfort and International Design: Predicting Thermal Comfort in Mixed-mode Office Building in the UK," Loughborough University, Jan. 18, 2019, 4 pages.

Sudhakaran et al., "Temperature, Relative Humidity, and Carbon-Dioxide Modulation in a Near-Zero Energy Efficient Retrofit House," Purdue University, 2016, 11 pages.

Weekly et al., "Modeling and Estimation of the Humans' Effect on the CO2 Dynamics Inside a Conference Room," IEEE Transactions On Control Systems Technology, Sep. 2015, 23.5, 12 pages.

International Search Report and Written Opinion on PCT/US2020/041792, dated Sep. 30, 15 pages.

Azimi et al., "HVAC filtration for controlling infectious airborne disease transmission in indoor environments: Predicting risk reductions and operational costs," Building and Environment May 13, 2013, 70, pp. 150-160.

International Search Report and Written Opinion on PCT/US2020/041770, dated Nov. 3, 2020, 13 pages.

International Search Report and Written Opinion on PCT/US2020/041845, dated Jan. 13, 2021, 20 pages.

Joe et al., "Methodology for Modeling the Microbial Contamination of Air Filters," PLoS ONE 9(2) e88514, URL: https://doi.org/10.1371/journal.pone.0088514, Feb. 11, 2014, 9 pages.

Kanaan et al., "New airborne pathogen transport model for upper-room UVGI spaces conditioned by chilled ceiling and mixed displacement ventilation: Enhancing air quality and energy performance," Energy Conversion and Management, Apr. 12, 2014, 85, pp. 50-61.

Liao et al., "A Probabilistic Transmission Dynamic Model to Assess Indoor Airborne Infection Risks," Risk Analysis, 2005, vol. 25, No. 5, pp. 1097-1107.

Noakes et al., "Applying the Wells-Riley equation to the risk of airborne infection in hospital environments: The importance of stochastic and proximity effects," Indoor Air 2008, The 11th Intl Conference on Indoor Air Quality and CI, Aug. 17-22, 2008, Copenhagen, Denmark, 9 pages.

Noakes et al., "Mathematical models for assessing the role of airflow on the risk of airborne infection in hospital wards," Journal of the Royal Society Interface, Jun. 2009, S791-S800, 10 pages.

Noakes et al., "Modelling the transmission of airborne infections in enclosed spaces," Epidemiol. Infect, 2006, vol. 134, pp. 1082-1091.

Stephens, "HVAC filtration and the Wells-Riley approach to assessing risks of infectious airborne diseases," The National Air Filtration Association (NAFA) Foundation, Mar. 1, 2012, 47 pages.

Sze et al., "Review and Comparison Between the Wells-Riley and Dose-Response Approaches to Risk Assessment of Infectious Respiratory Diseases," Indoor Air, 2010, 20, pp. 2-16.

Aliabadi et al., "Preventing Airborne Disease Transmission: Review of Methods for Ventilation Design in Health Care Facilities," SAGE—Hindawi Access to Research Advances in Preventive Medicine, Feb. 2011, vol. 2011, 21 pages.

Azimi et al., "HVAC filtration for controlling infectious airborne disease transmission in indoor environments: Predicting risk reductions and operational costs," Building and Environment, May 2013, 70, pp. 150-160.

Ching, "An empirical drag coefficient model for simulating the dispersion and deposition of bioaerosol particles in ventilated environments," The Hong Kong Polytechnic University Department of Building Services Engineering, Jun. 2016, 345 pages.

Copeland, "The Impact of Patient Room Design on Airborne Hospital-Acquired Infections (HAI)," Thesis, Kent State University, Degree of Masters of Science in Architecture and Environmental Design, May 2016, 61 pages.

Kumar, "A Simulation Framework to Characterize the Effect of Ventilation Control on Airborne Infectious Disease Transmission in Schools," Thesis, Graduate School of The University of Texas at Austin, May 2019, 53 pages.

Stephens, "HVAC filtration and the Wells-Riley approach to assessing risks of infectious airborne diseases," Wells-Riley & HVAC Filtration for infectious airborne aerosols, NAFA Foundation Report, Mar. 2013, 47 pages.

\* cited by examiner

SYSTEMS AND METHODS FOR OPTIMIZING VENTILATION, FILTRATION, AND CONDITIONING SCHEMES FOR BUILDINGS

CROSS REFERENCE TO RELATED APPLICATION

This application claims the benefit of and priority to U.S. Provisional Patent Application No. 62/873,631 filed Jul. 12, 2019, the entire disclosure of which is incorporated by reference herein. This application also claims the benefit of and priority to U.S. Provisional Patent Application No. 63/044,906 filed Jun. 26, 2020, U.S. Provisional Patent Application No. 63/046,376 filed Jun. 30, 2020, and U.S. Provisional Patent Application No. 63/047,119 filed Jul. 1, 2020.

BACKGROUND

Conventional methods for optimizing air quality within a building employ methods of using fixed ventilation rates to improve the quality of air. This can include ventilating the air in a constant process regardless of the change in outdoor air quality. In the event that air within a building may need to be optimized, conventional methods may rely on allowing more outdoor air to enter the building. This may not necessarily optimize the air quality, as the type of filtering, feedback system for various characteristics of outdoor air quality, and predictive modeling is not implemented and/or monitored.

SUMMARY

One implementation of the present disclosure is a building management system (BMS) for filtering a fluid within a building. The system includes one or more sensors configured to measure one or more characteristics of a first fluid within an air duct of the BMS and measure one or more characteristics of a second fluid after the second fluid has been filtered. The system further includes a pollutant management system configured to receive data from the one or more sensors and control a filtration process, wherein the filtration process selects a filter of a plurality of filters based on a level of the one or more characteristics of the first fluid and the one or more characteristics of the second fluid.

In some embodiments, measuring the one or more characteristics of the first fluid within the air duct of the BMS comprises measuring at least one of a carbon dioxide, nitrous oxide, particulate matter, or ozone levels of the first fluid. In some embodiments, measuring the one or more characteristics of the second fluid after the second fluid has been filtered comprises measuring at least one of a carbon dioxide, nitrous oxide, particulate matter, or ozone levels of the second fluid. In some embodiments, measuring one or more characteristics of the first fluid is performed by a first set of sensors and measuring the one or more characteristics of the second fluid after the second fluid has been filtered is performed by a second set of sensors. In some embodiments, the first fluid is a pre-filtered fluid received in the air duct and the second fluid is a post-filtered supply fluid within the air duct or a post-filtered fluid within a building zone.

In some embodiments, the pollutant management system comprises a predictive model module configured to receive filter data from a one or more filtration sensors, the one or more filtration sensors configured to record the filter data of the plurality of filters within the filtration process, the filter data comprising data relating to the one or more characteristics of the fluid. In some embodiments, the predictive model module is further configured to determine when the selected filter will become inoperable. In some embodiments, the predictive model module is further configured to, upon determining when the selected filter will become inoperable, alter the filtration process. In some embodiments, the filtration process further selects the filter of the plurality of filters based on a change in the one or more characteristics from filtering the first fluid.

In some embodiments, selecting the filter of the plurality of filters includes selecting the filter of the plurality of filters in a single fluid path, wherein all of the first fluid is filtered in the single fluid path.

In some embodiments, selecting the filter of the plurality of filters includes selecting a path of a plurality of paths in the air duct for the fluid to flow. In some embodiments, each of the plurality of paths includes one of the plurality of filters. In some embodiments, filtering the first fluid is based on the selected path.

In some embodiments, the pollutant management system is further configured to compare the level of the one or more characteristics measured by the one or more sensors to a predetermined threshold, the level of the one or more characteristics based on measurements from the one or more sensors.

In some embodiments, the pollutant management system further includes a timing module configured to process the first fluid based on predetermined intervals of time, wherein processing includes filtering, heating, disinfecting, or cleaning.

Another implementation of the present disclosure is a controller for filtering a fluid within a building management system (BMS). The controller includes a processing circuit including one or more processors and memory. The memory storing instructions that, when executed by the one or more processors, cause the one or more processors to perform operations. The operations include receiving, via one or more sensors, a first set of sensor data of one or more characteristics of a first fluid within an air duct of the BMS. The operations further include receiving, via the one or more sensors, a second set of sensor data of one or more characteristics of a second fluid after the second fluid has been filtered. The operations further include providing control signals to a filtration process, wherein the filtration process selects a filter of a plurality of filters based on a level of the one or more characteristics of the first fluid and the one or more characteristics of the second fluid. The operations further include generating a model of the first fluid. The operations further include generating predictions based on the model, wherein the model is generated based on the first set of sensor data and the second set of sensor data.

In some embodiments, receiving the first set of sensor data of the one or more characteristics of the first fluid within the air duct includes measuring at least one of a carbon dioxide, nitrous oxide, particulate matter, or ozone levels of the first fluid. In some embodiments, receiving the second set of sensor data of the one or more characteristics of the second fluid after the second fluid has been filtered includes measuring at least one of a carbon dioxide, nitrous oxide, particulate matter, or ozone levels of the second fluid. In some embodiments, the first set of sensor data of the one or more characteristics of the first fluid is received by a first set of sensors and the second set of sensor data of the one or more characteristics of the second fluid is received by a second set of sensors. In some embodiments, the first fluid is a pre-filtered fluid received in the air duct and the second fluid is a post-filtered supply fluid within the air duct or a post-filtered fluid within a building zone.

In some embodiments, the operations further include receiving filter data from one or more filtration sensors, the one or more filtration sensors configured to record the filter data of the plurality of filters within the filtration process, the filter data comprising data relating to the one or more characteristics of the fluid. In some embodiments, the operations further include determining when the selected filter will become inoperable. In some embodiments, the operations further include, upon determining when the selected filter will become inoperable, altering the filtration process. In some embodiments, the filtration process further selects the filter of the plurality of filters based on a change in the one or more characteristics from filtering the first fluid.

In some embodiments, selecting the filter of the plurality of filters includes selecting the filter of the plurality of filters in a single fluid path, wherein all of the first fluid is filtered in the single fluid path.

In some embodiments, selecting the filter of the plurality of filters includes selecting a path of a plurality of paths in the air duct for the first fluid to flow, wherein each of the plurality of paths comprises one of the plurality of filters and filtering the first fluid based on the selected path.

In some embodiments, the operations further include comparing the level of the one or more characteristics to a predetermined threshold, the level of the one or more characteristics based on information from the first set of sensor data, the second set of sensor data, or both.

In some embodiments, the operations further include processing the first fluid based on predetermined intervals of time, wherein processing comprising filtering, heating, disinfecting, or cleaning.

Another implementation of the present disclosure is a method for filtering a first fluid within a building management system (BMS). The method includes receiving, via one or more sensors, a first set of sensor data of one or more characteristics of the first fluid within an air duct of the BMS. The method further includes receiving, via the one or more sensors, a second set of sensor data of one or more characteristics of a second fluid after the second fluid has been filtered. The method further includes providing control signals to a filtration process, wherein the filtration process selects a filter of a plurality of filters based on a level of the one or more characteristics of the first fluid and the one or more characteristics of the second fluid.

In some embodiments, receiving the first set of sensor data of the one or more characteristics of the first fluid within the air duct comprises measuring at least one of a carbon dioxide, nitrous oxide, particulate matter or ozone levels of the first fluid. In some embodiments, receiving the second set of sensor data of the one or more characteristics of the second fluid after the second fluid has been filtered comprises measuring at least one of a carbon dioxide, nitrous oxide, particulate matter, or ozone levels of the second fluid. In some embodiments, the first set of sensor data of the one or more characteristics of the first fluid is received by a first set of sensors and the second set of sensor data of the one or more characteristics of the second fluid is received by a second set of sensors. In some embodiments, the first fluid is a pre-filtered fluid received in the air duct and the second fluid is a post-filtered supply fluid within the air duct or a post-filtered fluid within a building zone.

In some embodiments, the method further includes receiving filter data from one or more filtration sensors, the one or more filtration sensors configured to record filter data of the plurality of filters within the filtration process, the filter data comprising data relating to the one or more characteristics of the first fluid. In some embodiments, the method further includes determining when the selected filter will become inoperable. In some embodiments, the method further includes, upon determining when the selected filter will become inoperable, altering the filtration process. In some embodiments, the filtration process further selects the filter of the plurality of filters based on a change in the one or more characteristics from filtering the first fluid.

In some embodiments, selecting the filter of the plurality of filters includes selecting a path of a plurality of paths in the air duct for the first fluid to flow, wherein each of the plurality of paths comprises one of the plurality of filters and filtering the first fluid based on the selected path.

In some embodiments, the method further includes comparing the level of the one or more characteristics of the first fluid to a predetermined threshold, the level of the one or more characteristics of the first fluid based on information from the first set of sensor data, the second set of sensor data, or both.

In some embodiments, the method further includes processing the first fluid based on predetermined intervals of time, wherein processing comprising filtering, heating, disinfecting, or cleaning.

DETAILED DESCRIPTION

Overview

Referring generally to the FIGURES, systems and method for optimizing air quality in buildings are shown, according to an exemplary embodiment. This may be performed by using localized outdoor air quality data (e.g., at building ventilation inputs, etc.) to determine optimum outdoor air requirements to satisfy and/or optimize indoor air quality. Local outdoor air quality could be used to determine the appropriate level of secondary filtering/conditioning/etc. where required/desired indoor air quality (IAQ) measurements cannot be met by unconditioned/filtered outdoor air (OA). This could also decrease cost associated with over-ventilation as the makeup air needs to be processed (e.g., heated, cooled, humidified, dehumidified, etc.).

Building Management System and HVAC System

Figure 1:
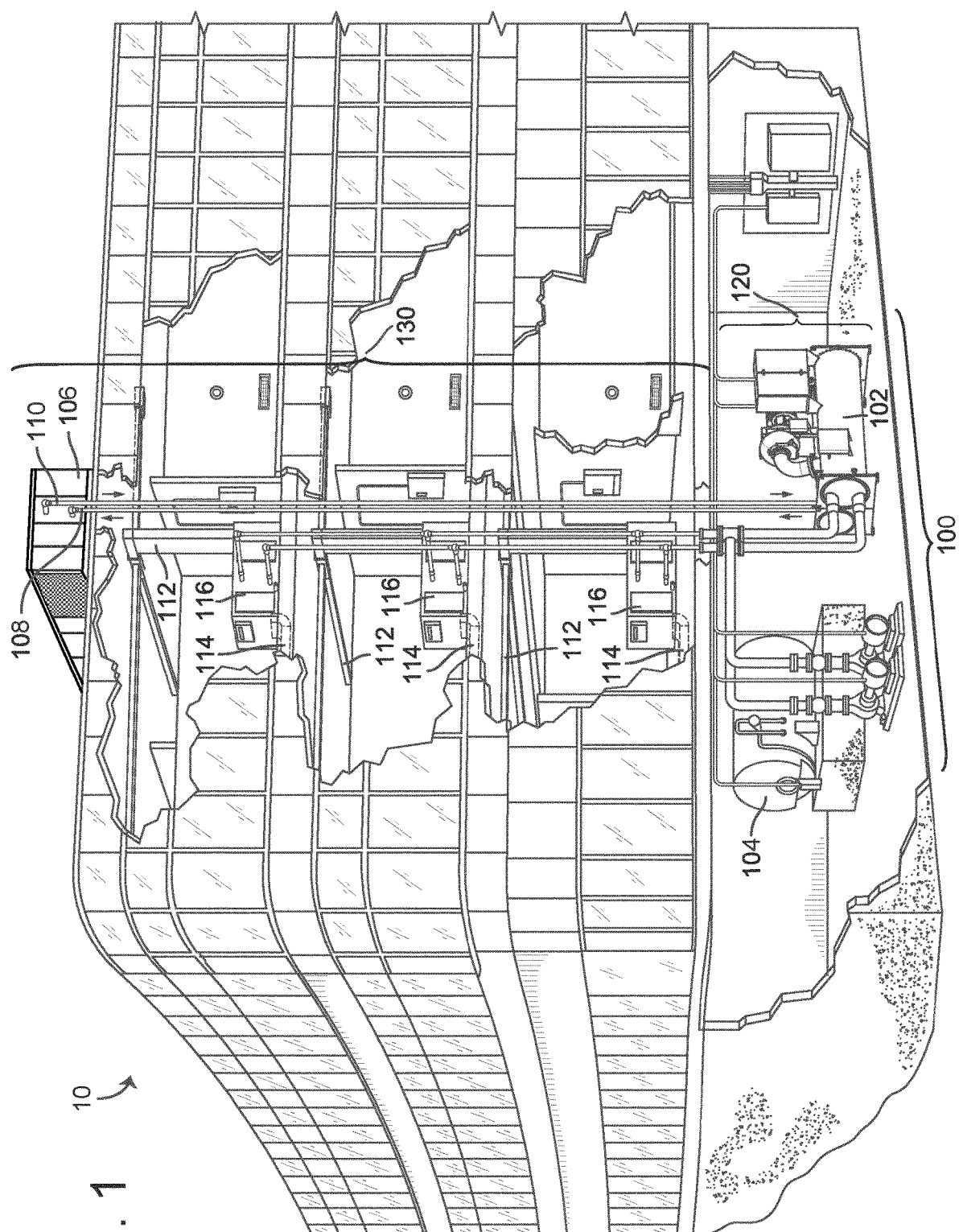
FIG. 1 is a drawing of a building equipped with a heating, ventilation, or air conditioning (HVAC) system, according to an exemplary embodiment.

Referring now to FIG. 1, a perspective view of a building 10 is shown. Building 10 is served by a building management system (BMS). A BMS is, in general, a system of devices configured to control, monitor, and manage equipment in or around a building or building area. A BMS can include, for example, a HVAC system, a security system, a lighting system, a fire alerting system, any other system that is capable of managing building functions or devices, or any combination thereof.

The BMS that serves building 10 includes an HVAC system 100. HVAC system 100 may include a plurality of HVAC devices (e.g., heaters, chillers, air handling units, pumps, fans, thermal energy storage, etc.) configured to provide heating, cooling, ventilation, or other services for building 10. For example, HVAC system 100 is shown to include a waterside system 120 and an airside system 130. Waterside system 120 may provide a heated or chilled fluid to an air handling unit of airside system 130. Airside system 130 may use the heated or chilled fluid to heat or cool an airflow provided to building 10. In some embodiments, waterside system 120 is replaced with a central energy plant such as central plant 200, described with reference to FIG. 2.

In some embodiments, building 10 acts as a building or campus (e.g., several buildings) capable of housing some or all components of HVAC system 100. While the systems and methods described herein are primarily focused on operations within a typical building (e.g., building 10), they can easily be applied to various other enclosures or spaces (e.g., cars, airplanes, recreational vehicles, etc.). For example, pollutant management system 502 as described below may be implemented in a recreational vehicle for filtering one or more fluids within the vehicle.

Still referring to FIG. 1, HVAC system 100 is shown to include a chiller 102, a boiler 104, and a rooftop air handling unit (AHU) 106. Waterside system 120 may use boiler 104 and chiller 102 to heat or cool a working fluid (e.g., water, glycol, etc.) and may circulate the working fluid to AHU 106. In various embodiments, the HVAC devices of waterside system 120 may be located in or around building 10 (as shown in FIG. 1) or at an offsite location such as a central plant (e.g., a chiller plant, a steam plant, a heat plant, etc.). The working fluid may be heated in boiler 104 or cooled in chiller 102, depending on whether heating or cooling is required in building 10. Boiler 104 may add heat to the circulated fluid, for example, by burning a combustible material (e.g., natural gas) or using an electric heating element. Chiller 102 may place the circulated fluid in a heat exchange relationship with another fluid (e.g., a refrigerant) in a heat exchanger (e.g., an evaporator) to absorb heat from the circulated fluid. The working fluid from chiller 102 and/or boiler 104 may be transported to AHU 106 via piping 108.

AHU 106 may place the working fluid in a heat exchange relationship with an airflow passing through AHU 106 (e.g., via one or more stages of cooling coils and/or heating coils). The airflow may be, for example, outside air, return air from within building 10, or a combination of both. AHU 106 may transfer heat between the airflow and the working fluid to provide heating or cooling for the airflow. For example, AHU 106 may include one or more fans or blowers configured to pass the airflow over or through a heat exchanger containing the working fluid. The working fluid may then return to chiller 102 or boiler 104 via piping 110.

Airside system 130 may deliver the airflow supplied by AHU 106 (i.e., the supply airflow) to building 10 via air supply ducts 112 and may provide return air from building 10 to AHU 106 via air return ducts 114. In some embodiments, airside system 130 includes multiple variable air volume (VAV) units 116. For example, airside system 130 is shown to include a separate VAV unit 116 on each floor or zone of building 10. VAV units 116 may include dampers or other flow control elements that can be operated to control an amount of the supply airflow provided to individual zones of building 10. In other embodiments, airside system 130 delivers the supply airflow into one or more zones of building 10 (e.g., via air supply ducts 112) without using intermediate VAV units 116 or other flow control elements. AHU 106 may include various sensors (e.g., temperature sensors, pressure sensors, etc.) configured to measure attributes of the supply airflow. AHU 106 may receive input from sensors located within AHU 106 and/or within the building zone and may adjust the flow rate, temperature, or other attributes of the supply airflow through AHU 106 to achieve setpoint conditions for the building zone.

Figure 2:
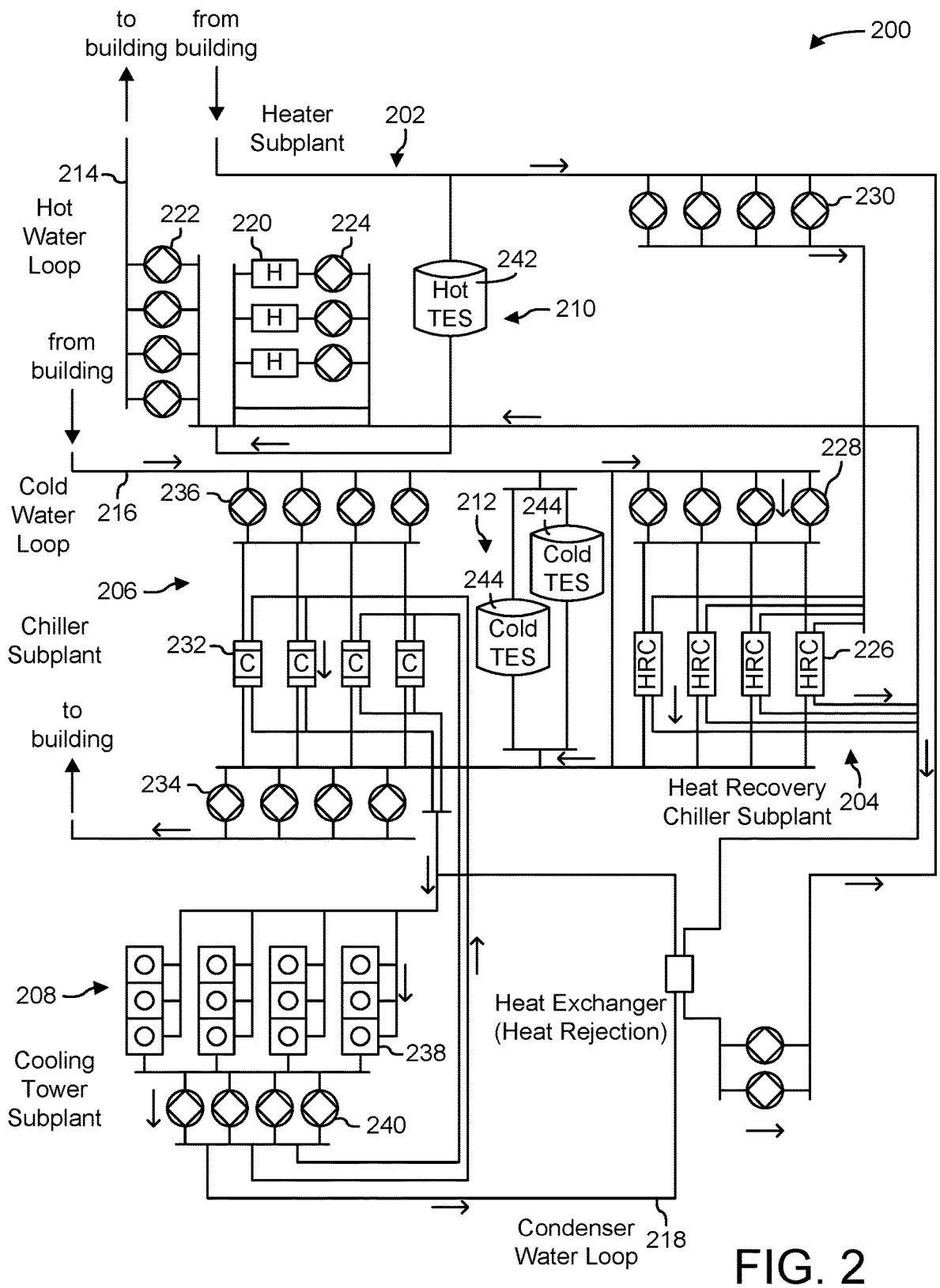
FIG. 2 is a schematic of a waterside system which can be used as part of the HVAC system of FIG. 1, according to some embodiments.

Referring now to FIG. 2, a block diagram of a central plant 200 is shown, according to an exemplary embodiment. In brief overview, central plant 200 may include various types of equipment configured to serve the thermal energy loads of a building or campus (i.e., a system of buildings). For example, central plant 200 may include heaters, chillers, heat recovery chillers, cooling towers, or other types of equipment configured to serve the heating and/or cooling loads of a building or campus. Central plant 200 may consume resources from a utility (e.g., electricity, water, natural gas, etc.) to heat or cool a working fluid that is circulated to one or more buildings or stored for later use (e.g., in thermal energy storage tanks) to provide heating or cooling for the buildings. In various embodiments, central plant 200 may supplement or replace waterside system 120 in building 10 or may be implemented separate from building 10 (e.g., at an offsite location).

Central plant 200 is shown to include a plurality of subplants 202-212 including a heater subplant 202, a heat recovery chiller subplant 204, a chiller subplant 206, a cooling tower subplant 208, a hot thermal energy storage (TES) subplant 210, and a cold thermal energy storage (TES) subplant 212. Subplants 202-212 consume resources from utilities to serve the thermal energy loads (e.g., hot water, cold water, heating, cooling, etc.) of a building or campus. For example, heater subplant 202 may be configured to heat water in a hot water loop 214 that circulates the hot water between heater subplant 202 and building 10. Chiller subplant 206 may be configured to chill water in a cold water loop 216 that circulates the cold water between chiller subplant 206 and building 10. Heat recovery chiller subplant 204 may be configured to transfer heat from cold water loop 216 to hot water loop 214 to provide additional heating for the hot water and additional cooling for the cold water. Condenser water loop 218 may absorb heat from the cold water in chiller subplant 206 and reject the absorbed heat in cooling tower subplant 208 or transfer the absorbed heat to hot water loop 214. Hot TES subplant 210 and cold TES subplant 212 may store hot and cold thermal energy, respectively, for subsequent use.

Hot water loop 214 and cold water loop 216 may deliver the heated and/or chilled water to air handlers located on the rooftop of building 10 (e.g., AHU 106) or to individual floors or zones of building 10 (e.g., VAV units 116). The air handlers push air past heat exchangers (e.g., heating coils or cooling coils) through which the water flows to provide heating or cooling for the air. The heated or cooled air may be delivered to individual zones of building 10 to serve the thermal energy loads of building 10. The water then returns to subplants 202-212 to receive further heating or cooling.

Although subplants 202-212 are shown and described as heating and cooling water for circulation to a building, it is understood that any other type of working fluid (e.g., glycol, $CO_2$, etc.) may be used in place of or in addition to water to serve the thermal energy loads. In other embodiments, subplants 202-212 may provide heating and/or cooling directly to the building or campus without requiring an intermediate heat transfer fluid. These and other variations to central plant 200 are within the teachings of the present invention.

Each of subplants 202-212 may include a variety of equipment configured to facilitate the functions of the subplant. For example, heater subplant 202 is shown to include a plurality of heating elements 220 (e.g., boilers, electric heaters, etc.) configured to add heat to the hot water in hot water loop 214. Heater subplant 202 is also shown to include several pumps 222 and 224 configured to circulate the hot water in hot water loop 214 and to control the flow rate of the hot water through individual heating elements 220. Chiller subplant 206 is shown to include a plurality of chillers 232 configured to remove heat from the cold water in cold water loop 216. Chiller subplant 206 is also shown to include several pumps 234 and 236 configured to circulate the cold water in cold water loop 216 and to control the flow rate of the cold water through individual chillers 232.

Heat recovery chiller subplant 204 is shown to include a plurality of heat recovery heat exchangers 226 (e.g., refrigeration circuits) configured to transfer heat from cold water loop 216 to hot water loop 214. Heat recovery chiller subplant 204 is also shown to include several pumps 228 and 230 configured to circulate the hot water and/or cold water through heat recovery heat exchangers 226 and to control the flow rate of the water through individual heat recovery heat exchangers 226. Cooling tower subplant 208 is shown to include a plurality of cooling towers 238 configured to remove heat from the condenser water in condenser water loop 218. Cooling tower subplant 208 is also shown to include several pumps 240 configured to circulate the condenser water in condenser water loop 218 and to control the flow rate of the condenser water through individual cooling towers 238.

Hot TES subplant 210 is shown to include a hot TES tank 242 configured to store the hot water for later use. Hot TES subplant 210 may also include one or more pumps or valves configured to control the flow rate of the hot water into or out of hot TES tank 242. Cold TES subplant 212 is shown to include cold TES tanks 244 configured to store the cold water for later use. Cold TES subplant 212 may also include one or more pumps or valves configured to control the flow rate of the cold water into or out of cold TES tanks 244.

In some embodiments, one or more of the pumps in central plant 200 (e.g., pumps 222, 224, 228, 230, 234, 236, and/or 240) or pipelines in central plant 200 include an isolation valve associated therewith. Isolation valves may be integrated with the pumps or positioned upstream or downstream of the pumps to control the fluid flows in central plant 200. In various embodiments, central plant 200 may include more, fewer, or different types of devices and/or subplants based on the particular configuration of central plant 200 and the types of loads served by central plant 200.

Figure 3:
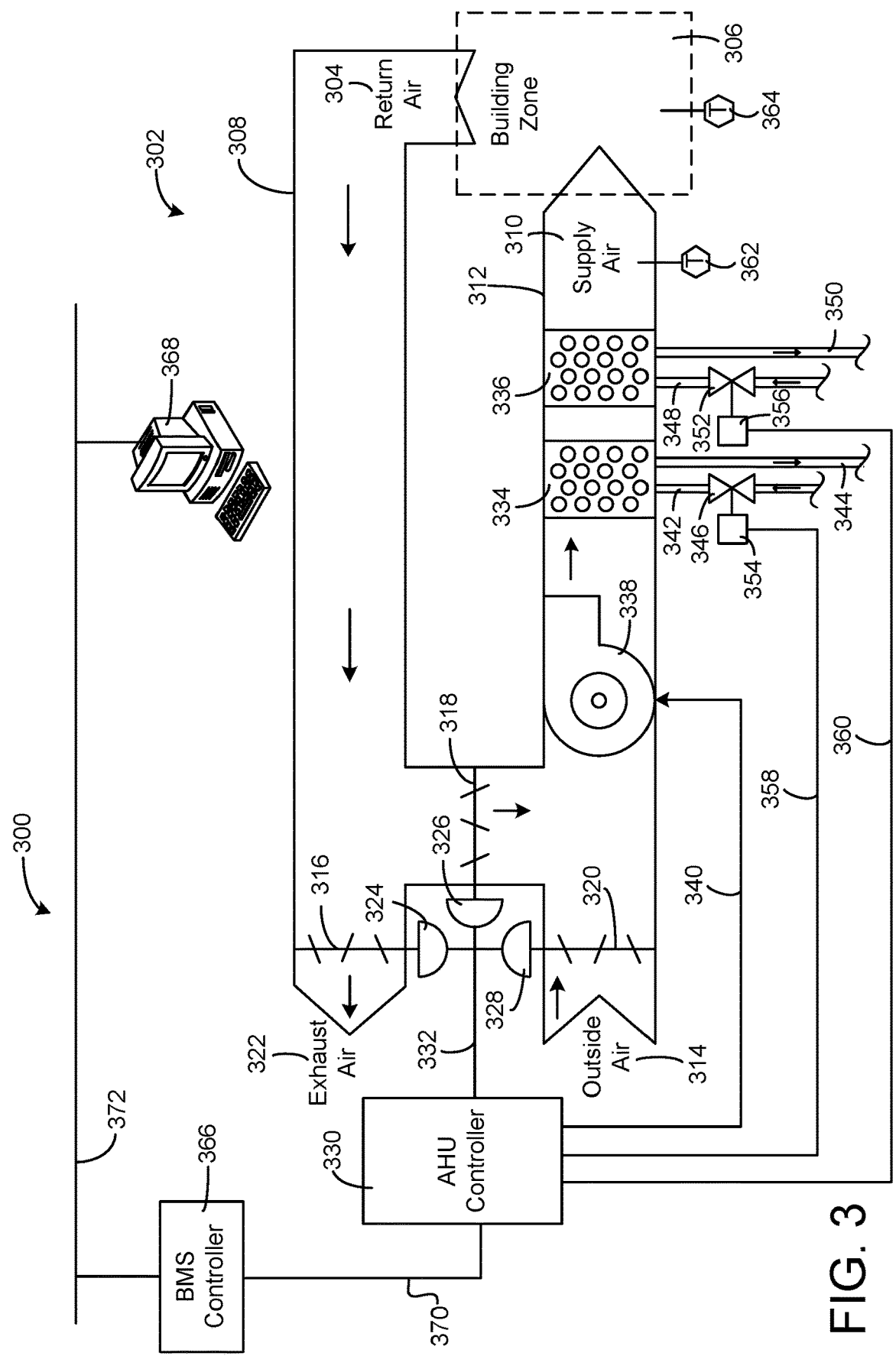
FIG. 3 is a block diagram of an airside system which can be used as part of the HVAC system of FIG. 1, according to some embodiments.

Referring now to FIG. 3, a block diagram of an airside system 300 is shown, according to an example embodiment. In various embodiments, airside system 300 can supplement or replace airside system 130 in HVAC system 100, or can be implemented separate from HVAC system 100. When implemented in HVAC system 100, airside system 300 can include a subset of the HVAC devices in HVAC system 100 (e.g., AHU 106, VAV units 116, duct 112, duct 114, fans, dampers, etc.) and can be located in or around building 10. Airside system 300 can operate to heat or cool an airflow provided to building 10 using a heated or chilled fluid provided by waterside system 200.

In FIG. 3, airside system 300 is shown to include an economizer-type air handling unit (AHU) 302. Economizer-type AHUs vary the amount of outside air and return air used by the air handling unit for heating or cooling. For example, AHU 302 can receive return air 304 from building zone 306 via return air duct 308 and can deliver supply air 310 to building zone 306 via supply air duct 312. In some embodiments, AHU 302 is a rooftop unit located on the roof of building 10 (e.g., AHU 106 as shown in FIG. 1) or otherwise positioned to receive both return air 304 and outside air 314. AHU 302 can be configured to operate exhaust air damper 316, mixing damper 318, and outside air damper 320 to control an amount of outside air 314 and return air 304 that combine to form supply air 310. Any return air 304 that does not pass through mixing damper 318 can be exhausted from AHU 302 through exhaust damper 316 as exhaust air 322.

Each of dampers 316-320 can be operated by an actuator. For example, exhaust air damper 316 can be operated by actuator 324, mixing damper 318 can be operated by actuator 326, and outside air damper 320 can be operated by actuator 328. Actuators 324-328 can communicate with an AHU controller 330 via a communications link 332. Actuators 324-328 can receive control signals from AHU controller 330 and can provide feedback signals to AHU controller 330. Feedback signals can include, for example, an indication of a current actuator or damper position, an amount of torque or force exerted by the actuator, diagnostic information (e.g., results of diagnostic tests performed by actuators 324-328), status information, commissioning information, configuration settings, calibration data, and/or other types of information or data that can be collected, stored, or used by actuators 324-328. AHU controller 330 can be an economizer controller configured to use one or more control algorithms (e.g., state-based algorithms, extremum seeking control (ESC) algorithms, proportional-integral (PI) control algorithms, proportional-integral-derivative (PID) control algorithms, model predictive control (MPC) algorithms, feedback control algorithms, etc.) to control actuators 324-328.

Still referring to FIG. 3, AHU 302 is shown to include a cooling coil 334, a heating coil 336, and a fan 338 positioned within supply air duct 312. Fan 338 can be configured to force supply air 310 through cooling coil 334 and/or heating coil 336 and provide supply air 310 to building zone 306. AHU controller 330 can communicate with fan 338 via communications link 340 to control a flow rate of supply air 310. In some embodiments, AHU controller 330 controls an amount of heating or cooling applied to supply air 310 by modulating a speed of fan 338.

Cooling coil 334 can receive a chilled fluid from waterside system 200 (e.g., from cold water loop 216) via piping 342 and can return the chilled fluid to waterside system 200 via piping 344. Valve 346 can be positioned along piping 342 or piping 344 to control a flow rate of the chilled fluid through cooling coil 334. In some embodiments, cooling coil 334 includes multiple stages of cooling coils that can be independently activated and deactivated (e.g., by AHU controller 330, by BMS controller 366, etc.) to modulate an amount of cooling applied to supply air 310.

Heating coil 336 can receive a heated fluid from waterside system 200 (e.g., from hot water loop 214) via piping 348 and can return the heated fluid to waterside system 200 via piping 350. Valve 352 can be positioned along piping 348 or piping 350 to control a flow rate of the heated fluid through heating coil 336. In some embodiments, heating coil 336 includes multiple stages of heating coils that can be independently activated and deactivated (e.g., by AHU controller 330, by BMS controller 366, etc.) to modulate an amount of heating applied to supply air 310.

Each of valves 346 and 352 can be controlled by an actuator. For example, valve 346 can be controlled by actuator 354 and valve 352 can be controlled by actuator 356. Actuators 354-356 can communicate with AHU controller 330 via communications links 358-360. Actuators 354-356 can receive control signals from AHU controller 330 and can provide feedback signals to controller 330. In some embodiments, AHU controller 330 receives a measurement of the supply air temperature from a temperature sensor 362 positioned in supply air duct 312 (e.g., downstream of cooling coil 334 and/or heating coil 336). AHU controller 330 can also receive a measurement of the temperature of building zone 306 from a temperature sensor 364 located in building zone 306.

In some embodiments, AHU controller 330 operates valves 346 and 352 via actuators 354-356 to modulate an amount of heating or cooling provided to supply air 310 (e.g., to achieve a setpoint temperature for supply air 310 or to maintain the temperature of supply air 310 within a setpoint temperature range). The positions of valves 346 and 352 affect the amount of heating or cooling provided to supply air 310 by cooling coil 334 or heating coil 336 and may correlate with the amount of energy consumed to achieve a desired supply air temperature. AHU controller 330 can control the temperature of supply air 310 and/or building zone 306 by activating or deactivating coils 334-336, adjusting a speed of fan 338, or a combination of both.

Still referring to FIG. 3, airside system 300 is shown to include a building management system (BMS) controller 366 and a client device 368. BMS controller 366 can include one or more computer systems (e.g., servers, supervisory controllers, subsystem controllers, etc.) that serve as system level controllers, application or data servers, head nodes, or master controllers for airside system 300, waterside system 200, HVAC system 100, and/or other controllable systems that serve building 10. BMS controller 366 can communicate with multiple downstream building systems or subsystems (e.g., HVAC system 100, a security system, a lighting system, waterside system 200, etc.) via a communications link 370 according to like or disparate protocols (e.g., LON, BACnet, etc.). In various embodiments, AHU controller 330 and BMS controller 366 can be separate (as shown in FIG. 3) or integrated. In an integrated implementation, AHU controller 330 can be a software module configured for execution by a processor of BMS controller 366.

In some embodiments, AHU controller 330 receives information from BMS controller 366 (e.g., commands, setpoints, operating boundaries, etc.) and provides information to BMS controller 366 (e.g., temperature measurements, valve or actuator positions, operating statuses, diagnostics, etc.). For example, AHU controller 330 can provide BMS controller 366 with temperature measurements from temperature sensors 362 and 364, equipment on/off states, equipment operating capacities, and/or any other information that can be used by BMS controller 366 to monitor or control a variable state or condition within building zone 306.

Client device 368 can include one or more human-machine interfaces or client interfaces (e.g., graphical user interfaces, reporting interfaces, text-based computer interfaces, client-facing web services, web servers that provide pages to web clients, etc.) for controlling, viewing, or otherwise interacting with HVAC system 100, its subsystems, and/or devices. Client device 368 can be a computer workstation, a client terminal, a remote or local interface, or any other type of user interface device. Client device 368 can be a stationary terminal or a mobile device. For example, client device 368 can be a desktop computer, a computer server with a user interface, a laptop computer, a tablet, a smartphone, a PDA, or any other type of mobile or non-mobile device. Client device 368 can communicate with BMS controller 366 and/or AHU controller 330 via communications link 372.

Figure 4:
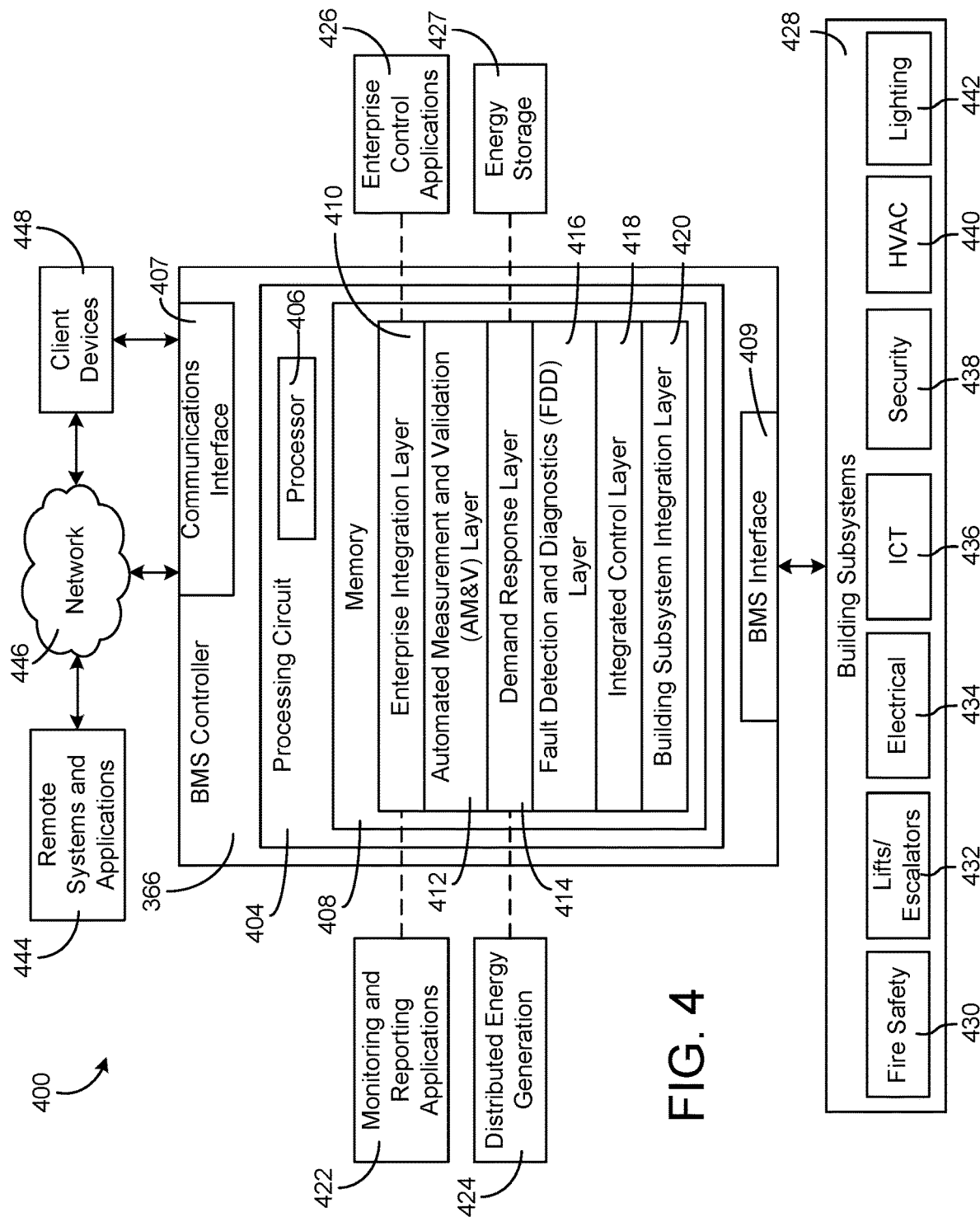
FIG. 4 is a block diagram of a building management system (BMS) which can be used in the building of FIG. 1, according to some embodiments.

Referring now to FIG. 4, a block diagram of a building management system (BMS) 400 is shown, according to an example embodiment. BMS 400 can be implemented in building 10 to automatically monitor and control various building functions. BMS 400 is shown to include BMS controller 366 and a plurality of building subsystems 428. Building subsystems 428 are shown to include a building electrical subsystem 434, an information communication technology (ICT) subsystem 436, a security subsystem 438, a HVAC subsystem 440, a lighting subsystem 442, a lift/escalators subsystem 432, and a fire safety subsystem 430. In various embodiments, building subsystems 428 can include fewer, additional, or alternative subsystems. For example, building subsystems 428 can also or alternatively include a refrigeration subsystem, an advertising or signage subsystem, a cooking subsystem, a vending subsystem, a printer or copy service subsystem, or any other type of building subsystem that uses controllable equipment and/or sensors to monitor or control building 10. In some embodiments, building subsystems 428 include waterside system 200 and/or airside system 300, as described with reference to FIGS. 2 and 3.

Each of building subsystems 428 can include any number of devices, controllers, and connections for completing its individual functions and control activities. HVAC subsystem 440 can include many of the same components as HVAC system 100, as described with reference to FIGS. 1-3. For example, HVAC subsystem 440 can include a chiller, a boiler, any number of air handling units, economizers, field controllers, supervisory controllers, actuators, temperature sensors, and other devices for controlling the temperature, humidity, airflow, or other variable conditions within building 10. Lighting subsystem 442 can include any number of light fixtures, ballasts, lighting sensors, dimmers, or other devices configured to controllably adjust the amount of light provided to a building space. Security subsystem 438 can include occupancy sensors, video surveillance cameras, digital video recorders, video processing servers, intrusion detection devices, access control devices (e.g., card access, etc.) and servers, or other security-related devices.

Still referring to FIG. 4, BMS controller 366 is shown to include a communications interface 407 and a BMS interface 409. Interface 407 can facilitate communications between BMS controller 366 and external applications (e.g., monitoring and reporting applications 422, enterprise control applications 426, remote systems and applications 444, applications residing on client devices 448, etc.) for allowing user control, monitoring, and adjustment to BMS controller 366 and/or subsystems 428. Interface 407 can also facilitate communications between BMS controller 366 and client devices 448. BMS interface 409 can facilitate communications between BMS controller 366 and building subsystems 428 (e.g., HVAC, lighting security, lifts, power distribution, business, etc.).

Interfaces 407, 409 can be or include wired or wireless communications interfaces (e.g., jacks, antennas, transmitters, receivers, transceivers, wire terminals, etc.) for conducting data communications with building subsystems 428 or other external systems or devices. In various embodiments, communications via interfaces 407, 409 can be direct (e.g., local wired or wireless communications) or via a communications network 446 (e.g., a WAN, the Internet, a cellular network, etc.). For example, interfaces 407, 409 can include an Ethernet card and port for sending and receiving data via an Ethernet-based communications link or network. In another example, interfaces 407, 409 can include a Wi-Fi transceiver for communicating via a wireless communications network. In another example, one or both of interfaces 407, 409 can include cellular or mobile phone communications transceivers. In one embodiment, communications interface 407 is a power line communications interface and BMS interface 409 is an Ethernet interface. In other embodiments, both communications interface 407 and BMS interface 409 are Ethernet interfaces or are the same Ethernet interface.

Still referring to FIG. 4, BMS controller 366 is shown to include a processing circuit 404 including a processor 406 and memory 408. Processing circuit 404 can be communicably connected to BMS interface 409 and/or communications interface 407 such that processing circuit 404 and the various components thereof can send and receive data via interfaces 407, 409. Processor 406 can be implemented as a general purpose processor, an application specific integrated circuit (ASIC), one or more field programmable gate arrays (FPGAs), a group of processing components, or other suitable electronic processing components.

Memory 408 (e.g., memory, memory unit, storage device, etc.) can include one or more devices (e.g., RAM, ROM, Flash memory, hard disk storage, etc.) for storing data and/or computer code for completing or facilitating the various processes, layers and modules described in the present application. Memory 408 can be or include volatile memory or non-volatile memory. Memory 408 can include database components, object code components, script components, or any other type of information structure for supporting the various activities and information structures described in the present application. According to an example embodiment, memory 408 is communicably connected to processor 406 via processing circuit 404 and includes computer code for executing (e.g., by processing circuit 404 and/or processor 406) one or more processes described herein.

In some embodiments, BMS controller 366 is implemented within a single computer (e.g., one server, one housing, etc.). In various other embodiments BMS controller 366 can be distributed across multiple servers or computers (e.g., that can exist in distributed locations). Further, while FIG. 4 shows applications 422 and 426 as existing outside of BMS controller 366, in some embodiments, applications 422 and 426 can be hosted within BMS controller 366 (e.g., within memory 408).

Still referring to FIG. 4, memory 408 is shown to include an enterprise integration layer 410, an automated measurement and validation (AM&V) layer 412, a demand response (DR) layer 414, a fault detection and diagnostics (FDD) layer 416, an integrated control layer 418, and a building subsystem integration later 420. Layers 410-420 can be configured to receive inputs from building subsystems 428 and other data sources, determine optimal control actions for building subsystems 428 based on the inputs, generate control signals based on the optimal control actions, and provide the generated control signals to building subsystems 428. The following paragraphs describe some of the general functions performed by each of layers 410-420 in BMS 400.

Enterprise integration layer 410 can be configured to serve clients or local applications with information and services to support a variety of enterprise-level applications. For example, enterprise control applications 426 can be configured to provide subsystem-spanning control to a graphical user interface (GUI) or to any number of enterprise-level business applications (e.g., accounting systems, user identification systems, etc.). Enterprise control applications 426 can also or alternatively be configured to provide configuration GUIs for configuring BMS controller 366. In yet other embodiments, enterprise control applications 426 can work with layers 410-420 to optimize building performance (e.g., efficiency, energy use, comfort, or safety) based on inputs received at interface 407 and/or BMS interface 409.

Building subsystem integration layer 420 can be configured to manage communications between BMS controller 366 and building subsystems 428. For example, building subsystem integration layer 420 can receive sensor data and input signals from building subsystems 428 and provide output data and control signals to building subsystems 428. Building subsystem integration layer 420 can also be configured to manage communications between building subsystems 428. Building subsystem integration layer 420 translate communications (e.g., sensor data, input signals, output signals, etc.) across a plurality of multi-vendor/multi-protocol systems.

Demand response layer 414 can be configured to optimize resource usage (e.g., electricity use, natural gas use, water use, etc.) and/or the monetary cost of such resource usage in response to satisfy the demand of building 10. The optimization can be based on time-of-use prices, curtailment signals, energy availability, or other data received from utility providers, distributed energy generation systems 424, from energy storage 427 (e.g., hot TES 242, cold TES 244, etc.), or from other sources. Demand response layer 414 can receive inputs from other layers of BMS controller 366 (e.g., building subsystem integration layer 420, integrated control layer 418, etc.). The inputs received from other layers can include environmental or sensor inputs such as temperature, carbon dioxide levels, relative humidity levels, air quality sensor outputs, occupancy sensor outputs, room schedules, and the like. The inputs can also include inputs such as electrical use (e.g., expressed in kWh), thermal load measurements, pricing information, projected pricing, smoothed pricing, curtailment signals from utilities, and the like.

According to an example embodiment, demand response layer 414 includes control logic for responding to the data and signals it receives. These responses can include communicating with the control algorithms in integrated control layer 418, changing control strategies, changing setpoints, or activating/deactivating building equipment or subsystems in a controlled manner. Demand response layer 414 can also include control logic configured to determine when to utilize stored energy. For example, demand response layer 414 can determine to begin using energy from energy storage 427 just prior to the beginning of a peak use hour.

In some embodiments, demand response layer 414 includes a control module configured to actively initiate control actions (e.g., automatically changing setpoints) which minimize energy costs based on one or more inputs representative of or based on demand (e.g., price, a curtailment signal, a demand level, etc.). In some embodiments, demand response layer 414 uses equipment models to determine an optimal set of control actions. The equipment models can include, for example, thermodynamic models describing the inputs, outputs, and/or functions performed by various sets of building equipment. Equipment models can represent collections of building equipment (e.g., subplants, chiller arrays, etc.) or individual devices (e.g., individual chillers, heaters, pumps, etc.).

Demand response layer 414 can further include or draw upon one or more demand response policy definitions (e.g., databases, XML files, etc.). The policy definitions can be edited or adjusted by a user (e.g., via a graphical user interface) so that the control actions initiated in response to demand inputs can be tailored for the user's application, desired comfort level, particular building equipment, or based on other concerns. For example, the demand response policy definitions can specify which equipment can be turned on or off in response to particular demand inputs, how long a system or piece of equipment should be turned off, what setpoints can be changed, what the allowable set point adjustment range is, how long to hold a high demand setpoint before returning to a normally scheduled setpoint, how close to approach capacity limits, which equipment modes to utilize, the energy transfer rates (e.g., the maximum rate, an alarm rate, other rate boundary information, etc.) into and out of energy storage devices (e.g., thermal storage tanks, battery banks, etc.), and when to dispatch on-site generation of energy (e.g., via fuel cells, a motor generator set, etc.).

Integrated control layer 418 can be configured to use the data input or output of building subsystem integration layer 420 and/or demand response later 414 to make control decisions. Due to the subsystem integration provided by building subsystem integration layer 420, integrated control layer 418 can integrate control activities of the subsystems 428 such that the subsystems 428 behave as a single integrated supersystem. In an example embodiment, integrated control layer 418 includes control logic that uses inputs and outputs from a plurality of building subsystems to provide greater comfort and energy savings relative to the comfort and energy savings that separate subsystems could provide alone. For example, integrated control layer 418 can be configured to use an input from a first subsystem to make an energy-saving control decision for a second subsystem. Results of these decisions can be communicated back to building subsystem integration layer 420.

Integrated control layer 418 is shown to be logically below demand response layer 414. Integrated control layer 418 can be configured to enhance the effectiveness of demand response layer 414 by enabling building subsystems 428 and their respective control loops to be controlled in coordination with demand response layer 414. This configuration may advantageously reduce disruptive demand response behavior relative to conventional systems. For example, integrated control layer 418 can be configured to assure that a demand response-driven upward adjustment to the setpoint for chilled water temperature (or another component that directly or indirectly affects temperature) does not result in an increase in fan energy (or other energy used to cool a space) that would result in greater total building energy use than was saved at the chiller.

Integrated control layer 418 can be configured to provide feedback to demand response layer 414 so that demand response layer 414 checks that constraints (e.g., temperature, lighting levels, etc.) are properly maintained even while demanded load shedding is in progress. The constraints can also include setpoint or sensed boundaries relating to safety, equipment operating limits and performance, comfort, fire codes, electrical codes, energy codes, and the like. Integrated control layer 418 is also logically below fault detection and diagnostics layer 416 and automated measurement and validation layer 412. Integrated control layer 418 can be configured to provide calculated inputs (e.g., aggregations) to these higher levels based on outputs from more than one building subsystem.

Automated measurement and validation (AM&V) layer 412 can be configured to verify that control strategies commanded by integrated control layer 418 or demand response layer 414 are working properly (e.g., using data aggregated by AM&V layer 412, integrated control layer 418, building subsystem integration layer 420, FDD layer 416, or otherwise). The calculations made by AM&V layer 412 can be based on building system energy models and/or equipment models for individual BMS devices or subsystems. For example, AM&V layer 412 can compare a model-predicted output with an actual output from building subsystems 428 to determine an accuracy of the model.

Fault detection and diagnostics (FDD) layer 416 can be configured to provide ongoing fault detection for building subsystems 428, building subsystem devices (i.e., building equipment), and control algorithms used by demand response layer 414 and integrated control layer 418. FDD layer 416 can receive data inputs from integrated control layer 418, directly from one or more building subsystems or devices, or from another data source. FDD layer 416 can automatically diagnose and respond to detected faults. The responses to detected or diagnosed faults can include providing an alert message to a user, a maintenance scheduling system, or a control algorithm configured to attempt to repair the fault or to work around the fault.

FDD layer 416 can be configured to output a specific identification of the faulty component or cause of the fault (e.g., loose damper linkage) using detailed subsystem inputs available at building subsystem integration layer 420. In other example embodiments, FDD layer 416 is configured to provide "fault" events to integrated control layer 418 which executes control strategies and policies in response to the received fault events. According to an example embodiment, FDD layer 416 (or a policy executed by an integrated control engine or business rules engine) can shut down systems or direct control activities around faulty devices or systems to reduce energy waste, extend equipment life, or assure proper control response.

FDD layer 416 can be configured to store or access a variety of different system data stores (or data points for live data). FDD layer 416 can use some content of the data stores to identify faults at the equipment level (e.g., specific chiller, specific AHU, specific terminal unit, etc.) and other content to identify faults at component or subsystem levels. For example, building subsystems 428 can generate temporal (i.e., time-series) data indicating the performance of BMS 400 and the various components thereof. The data generated by building subsystems 428 can include measured or calculated values that exhibit statistical characteristics and provide information about how the corresponding system or process (e.g., a temperature control process, a flow control process, etc.) is performing in terms of error from its setpoint. These processes can be examined by FDD layer 416 to expose when the system begins to degrade in performance and alert a user to repair the fault before it becomes more severe.

Air Quality Optimization System

Figure 5:
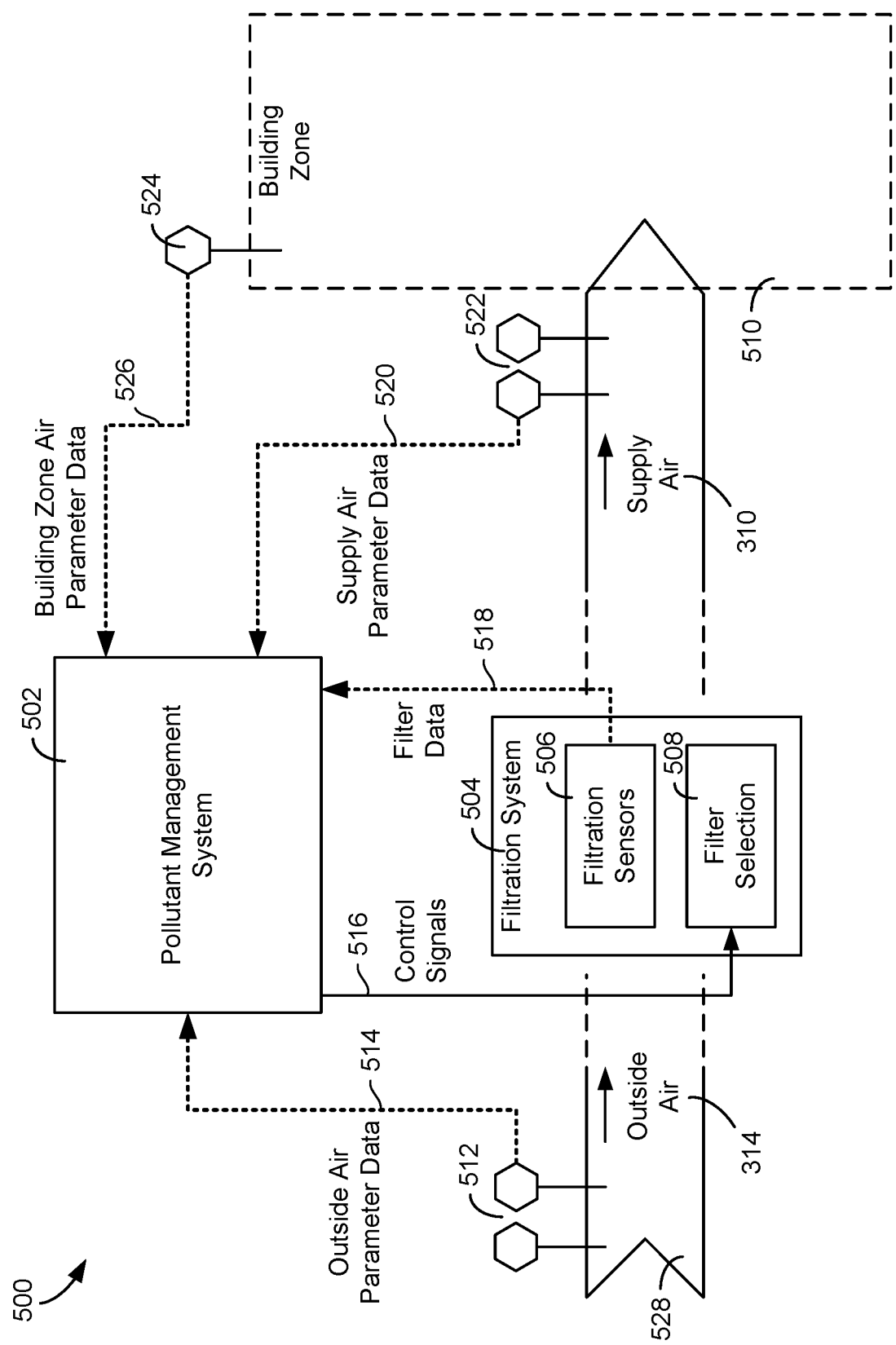
FIG. 5 is a block diagram of an air filtration system, which can be used in the BMS of FIG. 4, according to some embodiments.

Referring now to FIG. 5, system 500 is shown, according to an exemplary embodiment. System 500 may be configured to monitor various parameters of a fluid (e.g., air) and make control decisions based on the parameter measurements. For example, system 500 may monitor the quality of air with HVAC system 100 by monitoring various components of air, including: carbon dioxide (CO2), particle pollution (e.g., PM10-2.5, PM2.5, etc.), nitrous oxide (N2O), nitrogen dioxide (NO2) temperature, infectious bacteria, ozone ($O_3$), humidity, or any combination thereof. System 500 is shown to include pollutant management system 502, filtration system 504, building zone 510, outside air sensors 512, supply air sensors 522, building zone sensors 524, and air duct 528.

In a general embodiment, air may be received from outside of building 10 via one or more ventilation ducts to enter air duct 528. Various sensors (e.g., outside air sensors 512) may monitor the characteristics and/or quality of the entering air and provide the data to pollutant management system 502. The air is then selectively filtered based on control signals provided by pollutant management system 502, which are determined at least in part by the data received by outside air sensors 512. The filtered air (e.g., supply air 310) is then supplied to building zone 510 for building occupants. The characteristics and/or quality of supply air 310 are monitored by supply air sensors 522 and provided to pollutant management system 502 for processing. Additionally, the characteristics and/or quality of the air within building zone 510 are monitored by building zone sensors 524 and provided to pollutant management system 502 for processing. Pollutant management system 502 may receive the various sensor data and provide control signals to filtration system 504 for optimizing air quality. The control signals may be based on the sensor data from outside air 314, feedback from post-filtering sensors (e.g., supply air sensors 522, building zone sensors 524, etc.), or a combination of both.

Pollutant management system 502 may be configured to receive various sensor measurements (e.g., outside air parameter data 514, supply air parameter data 520, etc.) and provide control signals to selectively filter the air within air duct 528. For example, pollutant management system 502 may receive outside air parameter data 514 indicating that particulate matter (PM) (e.g., atmospheric aerosol particles) in the air are higher than normal. Pollutant management system 502 may then select a filter from filtration process 504 that is optimized for removing PM from air. Pollutant management system 502 is described in greater detail below with reference to FIG. 6.

Air duct 528 may be substantially similar or identical to supply air duct 312 as shown in FIG. 3. In some embodiments, air duct 528 includes features similar to the air handling features described in U.S. patent application Ser. No. 15/964,798, filed Apr. 4, 2018, the entire disclosure of which is incorporated by reference herein. Outside air 314 may refer to any type of fluid (e.g., air) that has been received from outside of building 10 and has not been filtered for pollutants and/or contaminants. Supply air 310 may refer to any type of fluid (e.g., air) that has been filtered for pollutants and/or contaminants.

Outside air sensors 512 may include one or more sensors configured to monitor air quality of outside air 314. In FIG. 5, outside air 310 is shown entering air duct 528 prior to being filtered by filtration system 504 and provide data on the characteristics and/or quality of outside air 314 to pollutant management system 502 for processing. Supply air sensors 522 may include one or more sensors configured to monitor air quality of supply air 310. In FIG. 5, supply air 310 is shown entering building zone 510 after being filtered by filtration system 504 and provide data on the characteristics and/or quality of supply air 310 to pollutant management system 502 for processing.

Filtration system 504 may be separate from pollutant management system 502 (as shown in FIG. 5) or incorporated entirely within pollutant management system 502. Filtration system 504 may be configured to receive control signals 516 that indicate which filtration method and/or process should be used to optimize the air quality within air duct 528. Filtration system 504 is shown to include filtration sensors 506 and filter selection 508.

Filtration sensors 506 may include a plurality of sensors for monitoring conditions of filters within air duct 528. In some embodiments, filtration sensors 506 monitor the conditions (e.g., characteristics, pollutants) of the filters within air duct 528 to determine the status of the filter (e.g., dirtiness, how full it is of pollutants, etc.). The sensors 506 may be located directly on the filters within filtration system 504 (e.g., on the edge of the filter) or may be located proximate to the filter (e.g., in the duct near the filter). In various embodiments, filtration sensors 506 are configured to measure carbon dioxide ($CO_2$), particle pollution (e.g., $PM_{10-2.5}$, $PM_{2.5}$, etc.), nitrous oxide ($N_2O$), temperature, infectious bacteria, ozone ($O_3$), particulate matter (PM), humidity, or any combination thereof. Filtration sensors 506 may provide filter data 518 to pollutant management system 502 for processing.

Filter selection 508 may be a module configured to select a filter for optimizing the air quality within air duct 528. In some embodiments, the process for determining which filter should be selected is performed in pollutant management system 502. In other embodiments, the processing is performed in filtration system 504. As described herein, "filters," may refer to any device for removing impurities or solid particles from a fluid (e.g., air). In a general embodiment, filters may refer to porous devices, such as the Multi-Pleat BOSS filters as sold by Koch Filters, Inc. In some embodiments, filter selection 508 includes selecting carbon filters, which may be ideal for filtering small particles. The carbon filters may use a bed of activated carbon to remove contaminants and impurities, using chemical absorption.

Building zone 510 may be any area or region of building 10 as shown in FIG. 1. In some embodiments, building zone 510 is a room (e.g., server room, meeting room, etc.), a floor (e.g., floor 5, floor 6, etc.), or a region (e.g., south-west corner of floor 5, east side of floor 6, etc.). Building zone 510 may include various sensors to monitor air quality within building zone 10, such as building zone sensor 524.

Building zone sensor 524 may include one or more sensors configured to monitor air quality within building zone 510. In FIG. 5, supply air 310 is shown entering building zone 510 after being filtered by filtration system 504. Building zone sensors 524 may monitor the characteristics of the air after supply air 310 has entered building zone 510. The air in building zone 510 may differ than the supply air 310 in air duct 528 as sunlight, occupants within building zone 510, open windows during a storm, and/or other external factors may gradually change the quality and/or content of the air within building zone 510. Building zone sensor 524 may monitor these characteristics and provide building zone air parameter data 526 to pollutant management system 502 for processing. While system 500 inlcudes various sensors (e.g., sensors 512, sensors 522) for measuring the fluid within duct 310, a couple or even a single sensor may be implemented to cover all or some of the air quality measuring performed by the various sensors within system 500.

Figure 6:
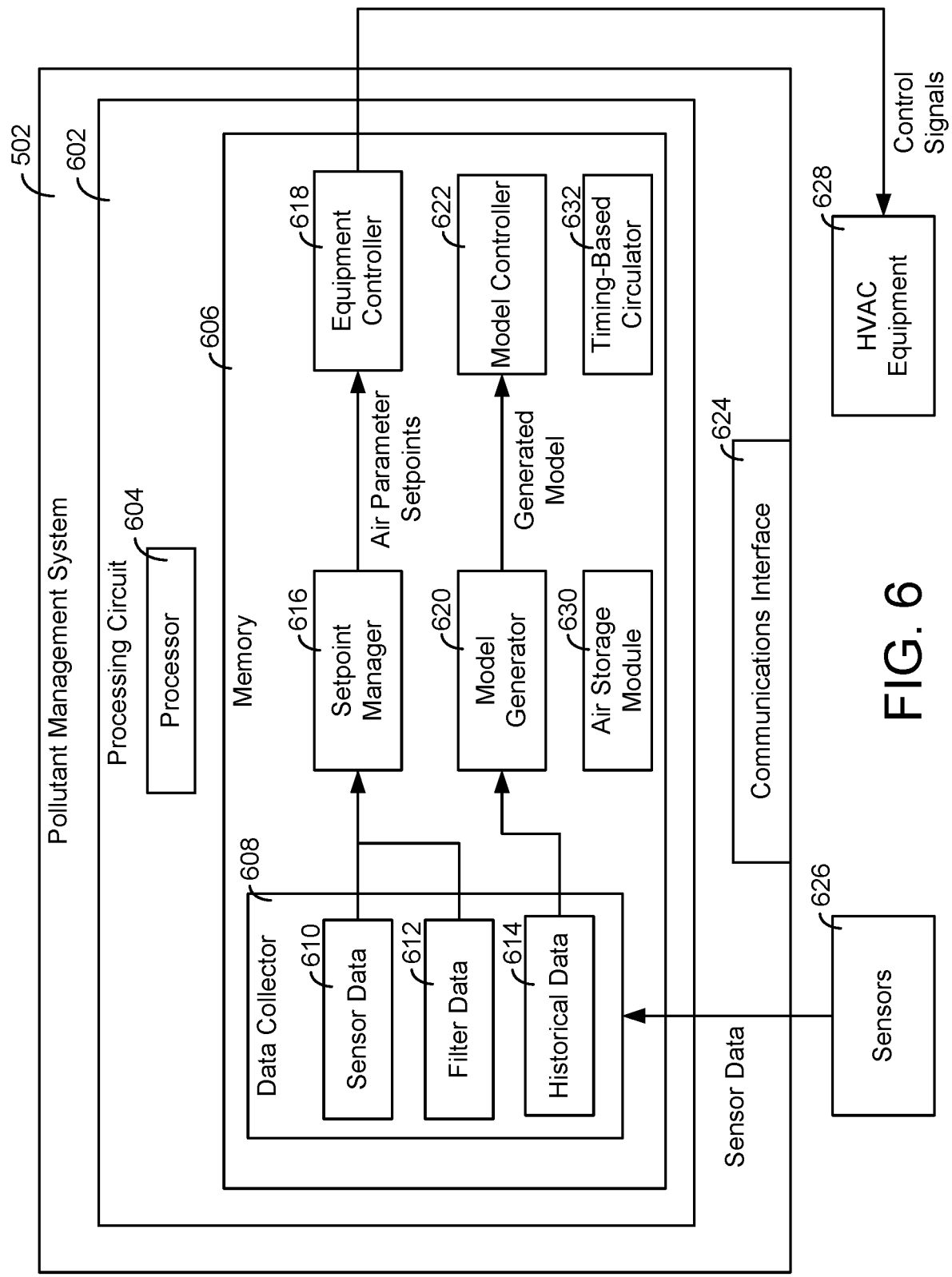
FIG. 6 is a detailed block diagram of a pollutant management system which can be used in the air filtration system of FIG. 5, according to some embodiments.

Referring now to FIG. 6, a block diagram of pollutant management system 502 is shown, according to an exemplary embodiment. Pollutant management system 502 is shown to include processing circuit 602, including processor 604 and memory 606. Processing circuit 602 can be communicably connected to BMS interface 409 and/or communications interface 624 such that processing circuit 604 and the various components thereof can send and receive data via interfaces 409, 624. Processor 604 can be implemented as a general purpose processor, an application specific integrated circuit (ASIC), one or more field programmable gate arrays (FPGAs), a group of processing components, or other suitable electronic processing components.

Memory 606 (e.g., memory, memory unit, storage device, etc.) can include one or more devices (e.g., RAM, ROM, Flash memory, hard disk storage, etc.) for storing data and/or computer code for completing or facilitating the various processes, layers and modules described in the present application. Memory 606 can be or include volatile memory or non-volatile memory. Memory 606 can include database components, object code components, script components, or any other type of information structure for supporting the various activities and information structures described in the present application. According to an example embodiment, memory 606 is communicably connected to processor 604 via processing circuit 602 and includes computer code for executing (e.g., by processing circuit 404 and/or processor 604) one or more processes described herein. In some embodiments, pollutant management system 502 is implemented within a single computer (e.g., one server, one housing, etc.). In various other embodiments pollutant management system 502 can be distributed across multiple servers or computers (e.g., that can exist in distributed locations).

Pollutant management system 502 is shown to include communications interface 624. Interface 624 can facilitate communications between pollutant management system 502 and external applications (e.g., filtration system 504, monitoring and reporting applications 422, enterprise control applications 426, remote systems and applications 444, applications residing on client devices 448, etc.) for allowing user control, monitoring, and adjustment to pollutant management system 502. Interface 624 can facilitate communications between pollutant management system 502 and building subsystems 428 (e.g., HVAC, lighting security, lifts, power distribution, business, etc.).

Interface 624 can be or include wired or wireless communications interfaces (e.g., jacks, antennas, transmitters, receivers, transceivers, wire terminals, etc.) for conducting data communications with building subsystems 428 or other external systems or devices. In various embodiments, communications via interface 624 can be direct (e.g., local wired or wireless communications) or via a communications network 446 (e.g., a WAN, the Internet, a cellular network, etc.). For example, interface 624 can include an Ethernet card and port for sending and receiving data via an Ethernet-based communications link or network. In another example, interface 624 can include a Wi-Fi transceiver for communicating via a wireless communications network. In another example, interface 624 can include cellular or mobile phone communications transceivers. Memory 606 is shown to include data collector 608, setpoint manager 616, equipment controller 618, model generator 620, and model controller 622.

Data collector 608 may be configured to collect various data from sensors within system 500 (e.g., outside air parameter data 514, supply air parameter data 520, etc. and provide data to setpoint manager 616 and/or model generator 620 for processing. Data collector 608 is shown to include sensor data 610, filter data 612, and historical data 614. Sensor data 610 may include the various data from sensors within system 500 (e.g., outside air parameter data 514, supply air parameter data 520, etc.). Filter data 612 may include data from filtration system 504 (e.g., filter data 518). Both sensor data 610 and filter data 612 may be used for determining a setpoint, as shown in FIG. 6.

Historical data 614 may include data representative of previous system parameters. For example, historical data 614 includes the data of how much nitrous oxide there was in the air within system 500 one year ago under similar weather conditions. In another example, historical data 614 includes data regarding the humidity levels during a storm, which may be used to forecast for an upcoming storm in the near future. Historical data 614 may include data from any time in the past relating to characteristics and/or quality of fluid flowing through air duct 528. Historical data 614 may also include data relating to weather or other parameters of BMS 400.

Setpoint manager 616 may be configured to determine various setpoints for HVAC equipment 628. Sensor data 610 and filter data 612 may be provided to setpoint manager 616 such that setpoint manager 616 can determine setpoints that will alter the data being received by data collector 608. For example, data collector 608 may receive sensor data indicating that carbon dioxide levels in outside air 314 are abnormally high (e.g., 10% higher than normal, 20% higher than normal, etc.). Setpoint manager 616 receives this data and determines that selecting two filters for absorbing carbon dioxide from supply air 314 should be implemented and provides setpoints for one or more actuators connected to the filters in filter selection 508 to equipment controller 618. Equipment controller 618 may be configured to receive setpoints and provide control signals to HVAC equipment 628. Equipment controller 618 and setpoint manager 616 may be combined into a single module and may not be separated as shown in FIG. 6. The various functionality performed by setpoint manager 616 may also be performed by equipment controller 618, and vice versa.

In some embodiments, data collector 608 may receive data indicating temperature levels of air within building zone 510 are within a suitable range (e.g., 19-24° C.) for operation of the system 500, but humidity levels in the air may be higher than normal (e.g., 65% humidity). Equipment controller 618 may receive this information and provide control signals to filtration system 504 to dehumidify the air. Accordingly, setpoint manager 616 may provide a humidity setpoint of 45% water-to-air setpoint to equipment controller 618 to attempt to reach. Supply air sensors 522 continue to monitor humidity levels of supply air 310 as feedback for equipment controller 618. Additionally, equipment controller 618, or any component within pollutant management system 502, may be receiving feedback from a variety of points throughout system 500 and are not limited to those shown in FIG. 5. Allowing for multiple feedback paths through various stages of the air filtering process advantageously allows for a dynamic control system that is able to detect problems at various stages and solve them dynamically (e.g., selecting the proper filter, etc.). In some embodiments, the feedback may be averaged to determine an average value for the sensor data. In other embodiments, the maximum values are used.

Model generator 620 may generate a model of air filtration system 500 based on historical data 614. Model generator 620 may then provide the model to model controller 622. Model controller 622 may then make control decisions based on the received model. For example, historical data 614 may indicate nitrous oxide levels increase in the outside air during the months of May-June, or around the time nitrogen-rich manure is used in crop fields. Model generator 620 may generate a model with the nitrous oxide data structure included in the model, and provide the model to model controller 622. Model controller 622 may then, upon preparation for an upcoming May-June period, provide additional nitrous oxide filtering within air duct 528. In some embodiments, model generator 620 may include various information that is not directly received from the sensors shown in FIG. 5. In some embodiments, model generator 620 (and in some cases, data collector 608), is receiving information relating to external factors changing temperatures within building zone 510 (e.g., sunlight, human heat, "Q other," etc.), CO2 generation within building zone 510, and other external variables.

Air storage module 630 may be configured to store fluid (e.g., bad air, good air, adequate air, etc.) to be further recirculated within air duct 528. In some embodiments, air storage module 630 stores used supply air from building zone 510 (e.g., within another duct, within a storage container, etc.) and provides the stored air back to air duct 528 based on instructions from pollutant management system 502. This may allow pollutant management system 502 to re-use supply air (e.g., supply air 310) without requiring the need to process (e.g., warm, filter, etc.) the air entirely. For example, the outside air 314 may come into air duct 528 at −15° C. (4° F.) and is warmed to a suitable temperature (e.g., 21° C. (70° F.), etc.) for building zone 510. Air storage module 630 may then store the used air from building zone 510 for a period of time (e.g., 1 minute, 5 minutes, 1 hour, 10 hours, etc.) to be re-used upon instruction from pollutant management system 502. The air may lose heat in storage but still be significantly higher in temperature (e.g., 10° C. (50° F.), etc.) compared to the received outside air of −15° C. In such an embodiment, system 500 may significantly save on energy costs when re-using air via air storage module 630.

Timing-based circulator 632 may be configured to circulate air within airside system 300 (or similarly system 500) based on timing criteria. For example, pollutant management system 502, BMS controller 366, AHU controller 330, or anything combination thereof, provides instructions to process the air (e.g., filter, warm, re-circulate) within air duct 308 after a period of time (e.g., 1 minute, 5 minutes, 10 minutes, 1 hour, 10 hours, etc.). In some embodiments, timing based circulator processes (e.g., filters, heats, cools, disinfects, cleans, etc.) the fluid based on predetermined intervals of time.

Sensors 626 may include the various sensors as shown in FIG. 5 (e.g., outside air sensors 512, supply air sensors 522, building zone sensors 524, etc.). Sensors 626 are not limited to the sensors disclosed herein and may include various other sensors within system 500. Sensors 626 provide sensor data to data collector 608. HVAC equipment 628 can include any HVAC equipment capable of changing one or more parameters within system 400 or system 500. HVAC equipment can include boilers, chillers, pumps, chilled fluid pipe valves, AHU dampers, and various other HVAC devices. HVAC equipment 628 can also include filtration system 504.

In some embodiments, air quality may be monitored via a user interface (not shown in FIG. 6). For example, a user interface may receive information regarding pollutant management system 502 via communications interface 624 and provide that information to a user. The user may then make control decisions (e.g., selecting filters, establishing setpoints, etc.) via the user interface. The user interface may then provide that information to pollutant management system 502 for implementation of the control decisions. The user interface may be located on a user device (e.g., smartphone, tablet, workplace computer, etc.) or directly on a device within system 500 (e.g., on air duct 528).

Figure 7A:
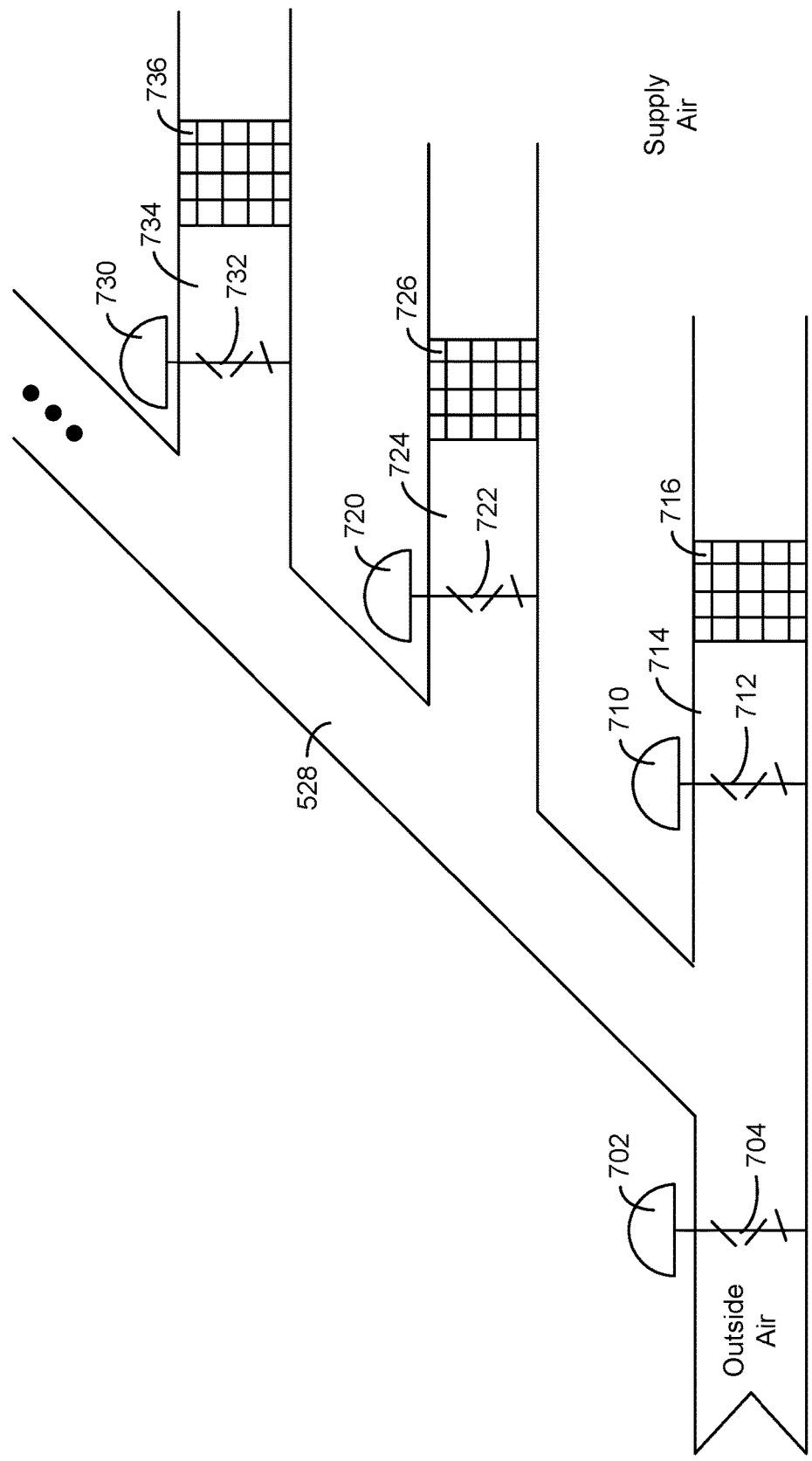
FIG. 7A is a diagram of an air duct unit that can be used in the air filtration system of FIG. 5, according to some embodiments.

Referring now to FIG. 7A, a diagram of air duct 528 is shown, according to an exemplary embodiment. FIG. 7A shows a method for selecting a filter that may be implemented by filtration system 504, particularly filter selection 508 in some embodiments. FIG. 7A is shown to include outside air (OA) actuator 702 and OA damper 704. FIG. 7A is further shown to include first actuator 710, first damper 712, and first filter 716 in first air path 714, second actuator 720, second damper 722, and second filter 726 in first air path 724, and third actuator 730, third damper 732, and third filter 736 in third path 734.

Figure 7B:
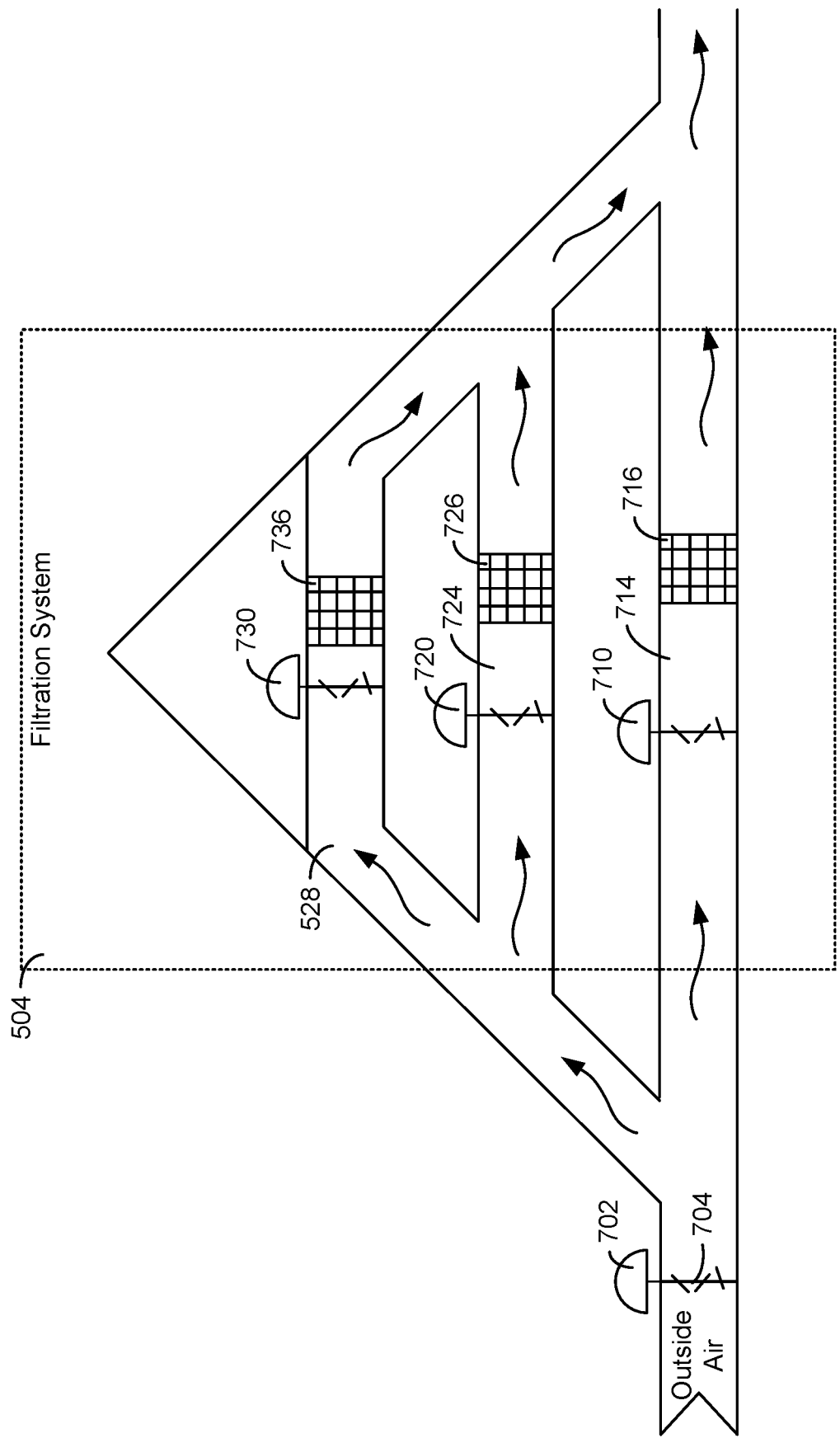
FIG. 7B is a diagram of an air duct unit that can be used in the air filtration system of FIG. 5, according to some embodiments.

The various actuators and dampers disclosed in FIGS. 7A-B are substantially similar or identical in functionality to actuators 324-328 and dampers 316-320, respectively. OA damper 704 may allow outside air to enter air duct 528. Air duct 528 is shown to include at least three different paths for allowing a fluid to flow. This may represent a method for selecting the filtering process, in contrast to having a single air path with varying filters in the single air path.

In some embodiments, a filter is located in front of damper 704 (e.g., preceding damper 704 within the path of the air) (not shown in FIG. 7A). In such an embodiment, this filter may be selected to filter out all of the air entering air duct 528. The air may be filtered exclusively by the filter in front of damper 704. In other embodiments, the filter in front of damper 704 filters the air initially, then the air is distributed to the various air duct paths for further filtering. For example, the filter in front of damper 704 may act as a general filter for various contaminants then, based on the specific particulate makeup of the air, the air may be distributed to separate air paths for more filtering.

Referring now to FIG. 7B, another diagram of air duct 528 is shown, according to an exemplary embodiment. FIG. 7B shows a possible flow path for fluid (e.g. air) flowing through air duct 528. The fluid may pass through one or more of the paths based on signals provided by pollutant management system 502. After the fluid passes through filtration system 504, the fluid returns back to a single path to be provided to the rest of the building (e.g., building zone 510).

Air Quality Optimization Processes

Figure 8:
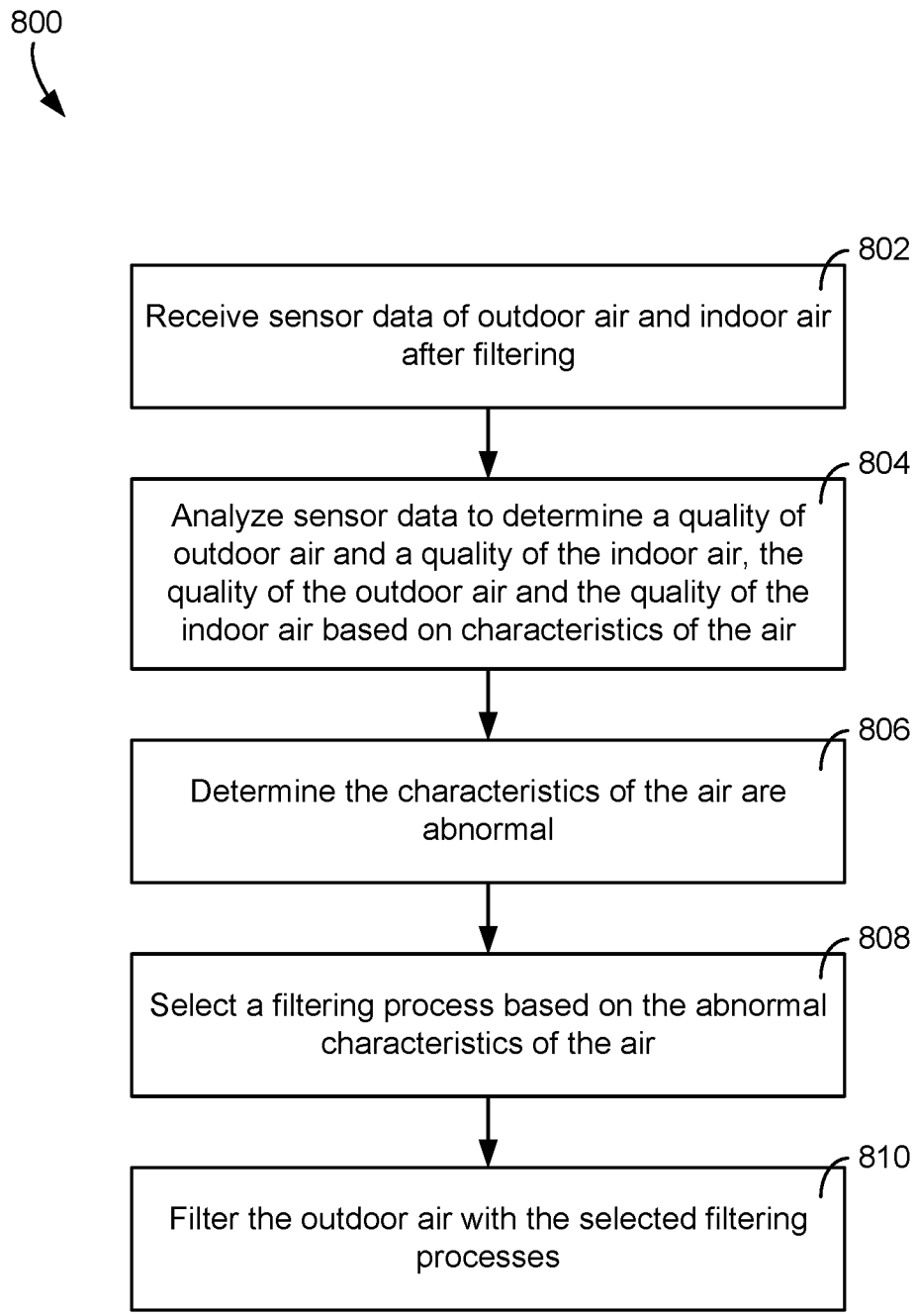
FIG. 8 is a process for optimizing outdoor air quality which may be performed by the system of FIG. 5, according to some embodiments.

Referring now to FIG. 8, a process 800 for optimizing air quality is shown, according to some embodiments. Process 800 may be performed by pollutant management system 502 as shown in FIG. 5.

Process 800 is shown to include receiving sensor data of outdoor air and indoor air after filtering (step 802). In some embodiments, pollutant management system 502 may receive sensor data on various characteristics of outdoor air and indoor air, including but not limited to carbon dioxide ($CO_2$), particle pollution (e.g., $PM_{10-2.5}$, $PM_{2.5}$, etc.), nitrous oxide ($N_2O$), temperature, infectious bacteria, ozone ($O_3$), particulate matter (PM), humidity, or any combination thereof. Step 802 may include receiving data from both outdoor air and indoor air to determine how the indoor air is changing after certain processes, such as filtering outdoor air and the indoor air being exposed to sunlight and CO2-emitting humans in a building.

Process 800 is shown to include analyzing sensor data to determine a quality of outdoor air and a quality of indoor air, the quality of the outdoor air and the quality of indoor air based on characteristics of the air (step 804). Step 804 refers to determining a set of characteristics regarding the air. For example, at a certain instance in time, the sensor data may include information on the CO2 levels in the air. At another instance in time, the sensor data may include information on the nitrous oxide levels in the air.

Process 800 is shown to include determining that the characteristics of the air are abnormal (step 806). In some embodiments, one or more thresholds are established for various levels for characteristics of the air. For example, a humidity threshold of 55% may be established, such that any sensor data of air that indicates a humidity threshold over 55% will signal abnormal characteristics of the air quality. Thresholds for some characteristics of the air may differ in values/ranges than thresholds for other characteristics of the air.

Process 800 is shown to include selecting a filtering process based on the abnormal characteristics of the air (step 808) and filtering the outdoor air with the selected filtering process (step 810). In the event that certain characteristics are determined to be at abnormal levels, a filtering process may be implemented, such as filtering system 504 as shown in FIG. 5. Filtering processes may differ in design (e.g., multi-filter single-path, single-filter multi-path, etc.) but may be configured to reduce/increase abnormal levels of one or more air quality characteristics to a normal operating range. For example, a nitrogen dioxide (NO2) filter may, upon pollutant management system 502 determining that NO2 levels were above a threshold level of 150 parts per billion (PPB), filter the NO2 out of outside air 314 until NO2 levels drop below 150 PPB.

In some embodiments, the air may be filtered by means of an ultra-violet (UV) filter to eliminate pollutants (e.g., germs, mold, mildew, bacteria, etc.). This may be performed by a UV light filter located within air duct 528, such as filter 726. For example, pollutant management system 502 may determine that bacteria levels were above a predetermined threshold level. Pollutant management system 502 may then select a path within air duct 528 to filter the air. In other embodiments, the UV light filters may be located in any and all paths within air duct 528.

In some embodiments, the filtering process may include chemical sprays, disinfectants, or other aerosols capable of filtering pollutants from the air. For example, filter 726 as shown in FIG. 7B includes a mechanism for spraying the air with one or more aerosols. The spray (e.g., aerosol, disinfectant, etc.) may sanitize and/or purify the air.

Figure 9:
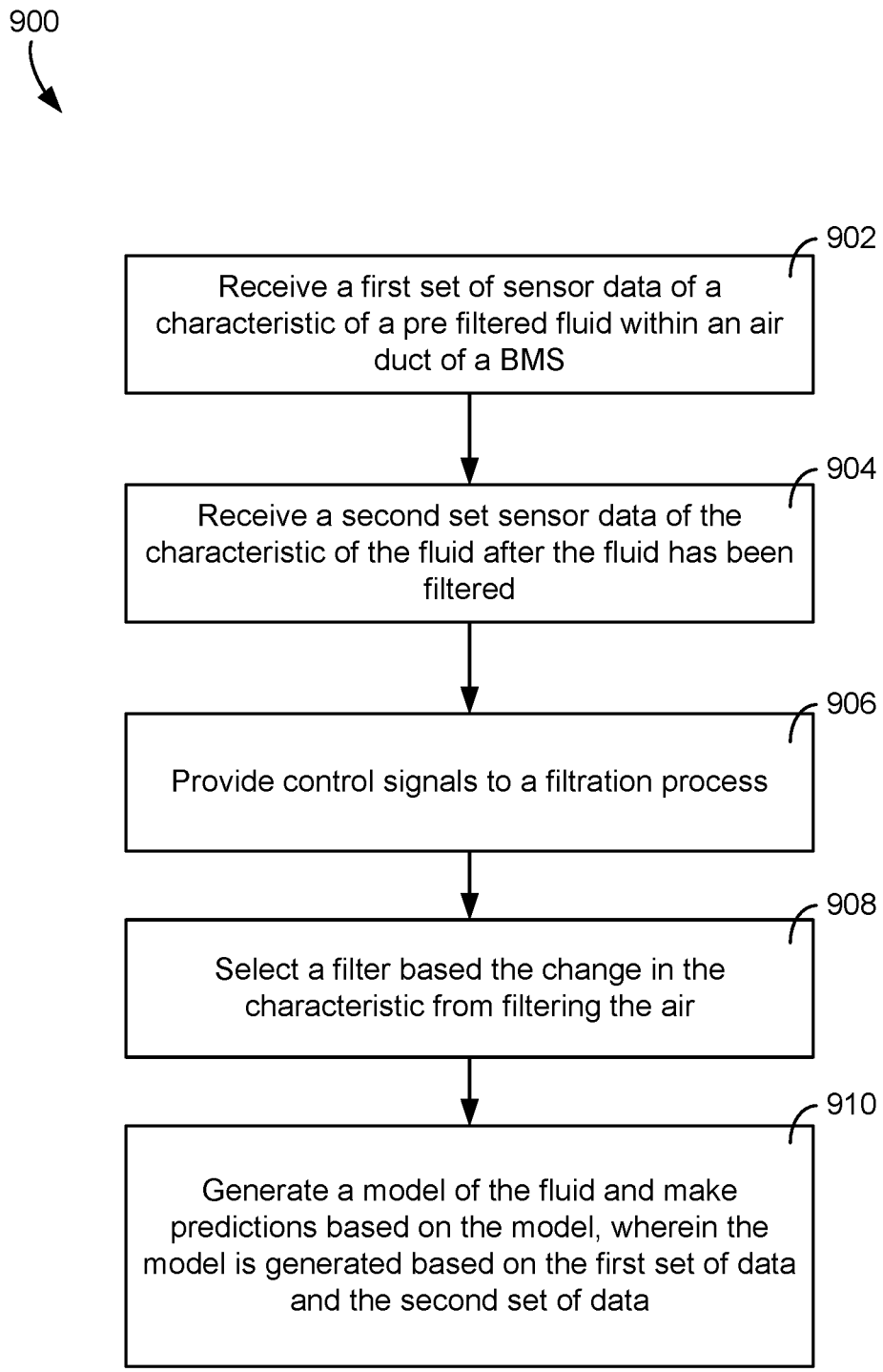
FIG. 9 is a process for optimizing outdoor air quality using predictive modeling which may be performed by the system of FIG. 5, according to some embodiments.

Referring now to FIG. 9, a process for optimizing air quality with predictive modeling is shown, according to exemplary embodiments. Process 900 may be performed by pollutant management system 502 as shown in FIG. 5. Process 900 is shown to include receiving a first set of sensor data of a characteristic of a pre-filtered fluid within an air duct of a BMS (step 902) and receiving a second set of sensor data of the characteristic of the fluid after the fluid has been filtered (step 904). Steps 902-904 may be similar to step 802 as shown in FIG. 8.

Process 900 is shown to include providing control signals to a filtration process (step 906). In some embodiments, the first and second data sets may indicate abnormal measurements (e.g., various abnormal characteristics as described in process 800) and a filtering process for the air may be implemented. Pollutant management system 502 may provide the control signals for filtering the air. Process 908 is shown to include selecting a filter based on the change in characteristic of the filtering air (step 908). This step may be similar to step 808 as shown in process 800.

Process 900 is shown to include generating a model of the fluid and making predictions based on the model, wherein the model is generated based on the first set of data and the second set of data (step 910). In some embodiments, pollutant management system 502 can receive training data that allows for the generation of a predictive model. The model may represent the makeup of the air at various time periods, seasons, locations, or any combination thereof. In some embodiments, pollutant management system 502 will make predictions based on the model, such as over-filtering the air for NO2 at a first instance in time, for preparation of a high increase in NO2 in an upcoming second instance in time (e.g., 3 days later, 5 days later, etc.).

Figure 10:
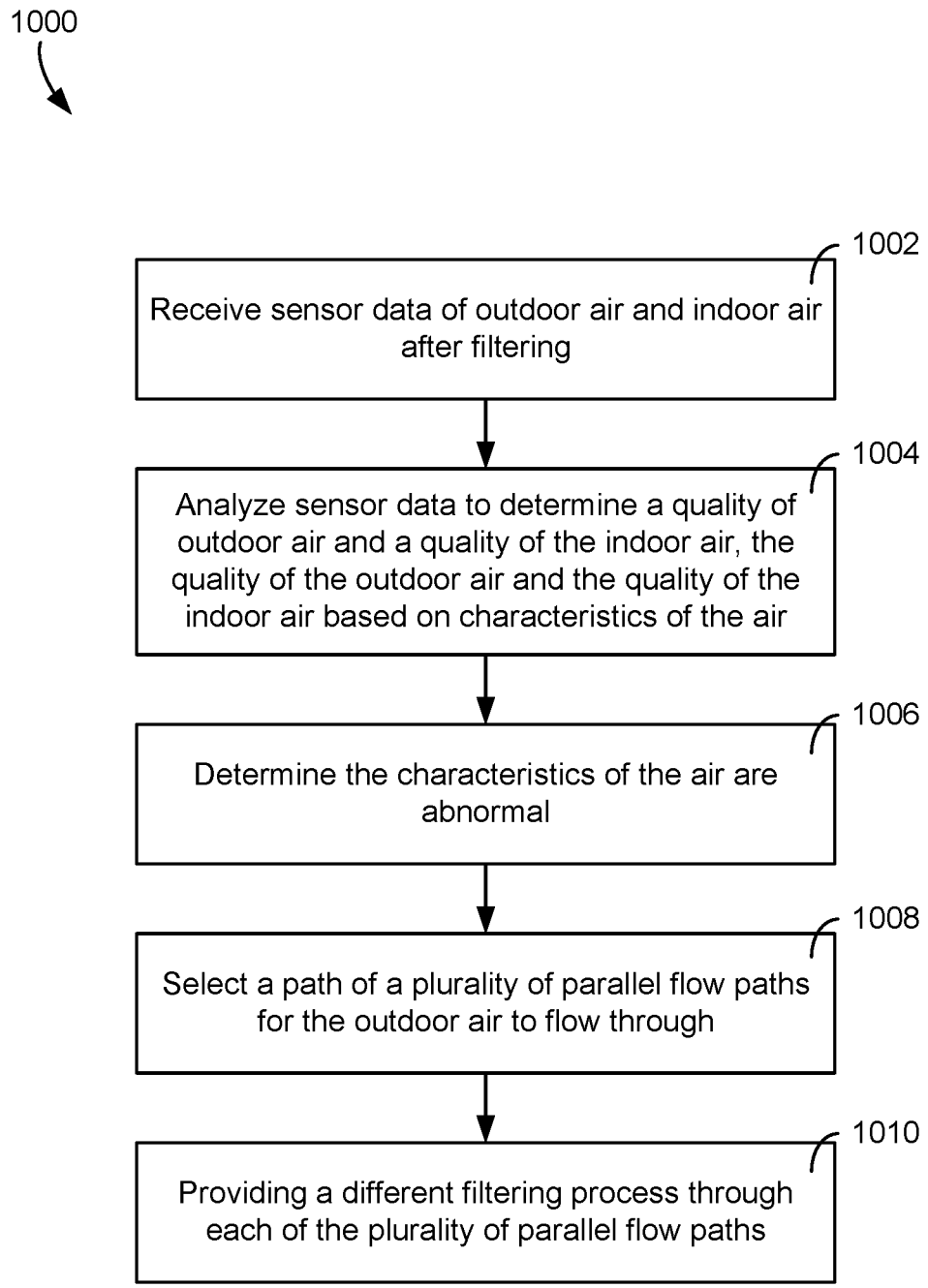
FIG. 10 is a process for optimizing outdoor air quality which may be performed by the system of FIG. 5, according to some embodiments.

Referring now to FIG. 10, a process 1000 for selectively filtering air using parallel flow paths is shown, according to exemplary embodiments. Process 1000 is shown to include receiving sensor data of outdoor air and indoor air after filtering (step 1002), analyzing sensor data to determine a quality of outdoor air and a quality of indoor air, the quality of the outdoor air and the quality of indoor air based on characteristics of the air (step 1004), and determining that the characteristics of the air are abnormal (step 1006). These steps may be substantially similar or identical to steps 802-806 as described above with reference to FIG. 8.

Process 1000 is shown to include selecting a path of a plurality of parallel flow paths for the outdoor air to flow through (step 1008) and providing a filtering process through each of the plurality of parallel flow paths (step 1010). In some embodiments, the filtering process is a multi-pathway (i.e., multi-path) system wherein each path includes an independent filtering process. For example, in the event that pollutant management system 502 receives an indication that NO2 levels are above a predetermined threshold, pollutant management system 502 may provide control signals such that outside air 314 flows through a first path, as the first path is optimized for removing NO2 particulates from the air. Later (e.g., 1 hour, 1 day, etc.) pollutant management system 502 receives an indication that PM levels are above a predetermined threshold and provides control signals such that outside air 314 flows through a second path optimized for removing PM.

In some embodiments, pollutant management system 502 facilitates model predictive control by describing how the temperature of building air and mass changes as the building is heated (or cooled). In some embodiments, the model describing these two temperatures is given by:

$$\dot{T}_z = \left(\frac{-1}{R_{im}C_a} - \frac{1}{R_{oa}C_{az}}\right)T_z + \frac{1}{R_{im}C_a}T_m + \frac{1}{R_{oa}C_a}T_{oa} + \frac{1}{C_a}\dot{Q}_{HVAC}\frac{1}{C_a}\dot{Q}_{Other}$$

$$\dot{T}_m = \frac{1}{R_{im}C_m}T_z - \frac{1}{R_{im}C_m}T_m$$

where $\dot{T}_z$ is a rate of change of temperature in a zone, $R_{im}$ is a mass thermal resistance value of a resistor (e.g., a wall, a door, etc.), $C_a$ is an capacitance value of air, $T_z$ is a temperature in the zone, $T_{oa}$ is an outdoor air temperature, $\dot{Q}_{HVAC}$ is an amount of heat contributed by a heat, ventilation, or air conditioning (HVAC) system, $\dot{Q}_{Other}$ is a heat transfer value, $\dot{T}_m$ is a rate of change in a building mass temperature, $C_m$ is a mass thermal capacitance value, and $T_m$ is a building mass temperature. By using the model, asset allocator 402 can capture the dynamic nature of a zone (or any space) of a building.

If a goal is to maintain comfort in regards to temperature and humidity as well as contaminates (e.g., PM2.5, PM10, etc.) in the air, the above model can be augmented with equations describing the additional states as follows:

$$\dot{T}_z = \left(\frac{-1}{R_{im}C_a} - \frac{1}{R_{oa}C_{a_z}}\right)T_z + \frac{1}{R_{im}C_a}T_m +$$

$$\frac{1}{R_{oa}C_a}T_{oa} + \frac{1}{C_a}\dot{Q}_{HVAC} + \frac{1}{C_a}\dot{Q}_{Other} + \dot{v}(T_{oa} - T_z)$$

$$\dot{T}_m = \frac{1}{R_{im}C_m}T_z - \frac{1}{R_{im}C_m}T_m$$

$$\dot{\varphi}_{H2O,in} = \dot{v}(\varphi_{H2O,out} - \varphi_{H2O,in}) + \dot{\varphi}_{H2O,dist} - \dot{\varphi}_{H2O,hvac} + \dot{\varphi}_{H2O,control}$$

$$\vdots$$

$$\dot{\varphi}_{X,in} = \dot{v}(\varphi_{X,out} - \varphi_{X,in}) + \dot{\varphi}_{X,dist} + \dot{\varphi}_{X,control}$$

where $\dot{\varphi}_{H2O,in}$ is a rate of change in a concentration of water in the air, $\dot{v}$ is an airflow normalized by a volume of air in a space (e.g., a zone), $\varphi_{X,out}$ is a concentration of water in the air outside of the space (e.g., in the outdoors), $\varphi_{X,in}$ is a concentration of water in the air inside the space $\dot{\varphi}_{H2O,dist}$ is a disturbance rate of water in the space $\dot{\varphi}_{H2O,hvac}$ is a rate of change of water in the air due to HVAC equipment operation, and $\dot{\varphi}_{H2O,control}$ is a rate of change of water in the air due to control decisions, $\dot{\varphi}_{X,in}$ is a rate of change in a concentration of a contaminant in the air, $\varphi_{X,out}$ is a concentration of the contaminant in the air outside of the space, $\varphi_{X,in}$ is a concentration of contaminant in the air inside the space, $\dot{\varphi}_{X,dist}$ is a disturbance rate of the contaminant in the space $\dot{\varphi}_{X,control}$ is a rate of change of the contaminant in the air due to control decisions, and all other variables are the same as described above. In general, the model can be augmented with additional contaminants as necessary for the optimization problem. The optimization processes described above may be similar to the optimization processes described in U.S. patent application Ser. No. 16/703,514 filed Dec. 4, 2019, the entire disclosure of which is incorporated herein.

Figure 11:
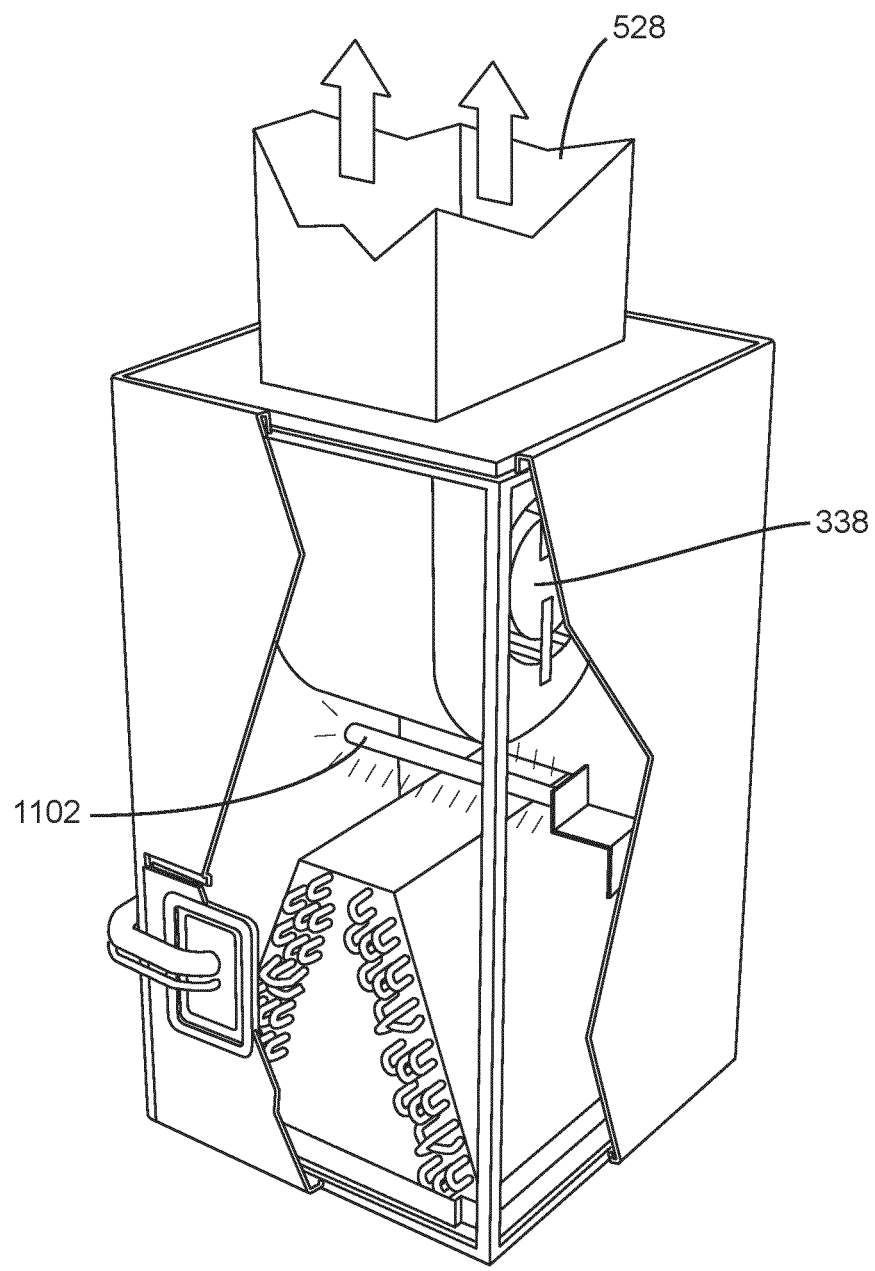
FIG. 11 is a diagram of filtering air in an air duct, which may be performed by the system of FIG. 5, according to some embodiments.

Referring now to FIG. 11, a diagram for filtering air within air duct 528 is shown, according to exemplary embodiments. FIG. 11 shows UV filter 1102 filtering air and fan 338 blowing the air farther into air duct 528 (e.g., into building 10). In some embodiments, UV filter 1102 is filtering out pollutants capable of being eliminated by ultraviolet light. For example, UV filter 1102 may be filtering out bacteria or mold from within the air.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with

What is claimed is:

1. A building management system (BMS) for filtering a fluid within a building, the system comprising:
   one or more sensors configured to:
   measure one or more characteristics of a first fluid within an air duct of the BMS; and
   measure one or more characteristics of a second fluid after the second fluid has been filtered; and
   wherein the first fluid is a pre-filtered fluid received in the air duct and the second fluid is a post-filtered supply fluid within the air duct or a post-filtered fluid within a building zone; and
   a pollutant management system comprising a processing circuit comprising one or more processors and memory storing instructions that, when executed by the one or more processors, cause the one or more processors to perform operations comprising:
   receiving data from the one or more sensors; and
   selecting a filter from at least a first filter of a first type or a second filter of a second type different than the first type based on a level of the one or more characteristics of the first fluid and the one or more characteristics of the second fluid, the first filter of the first type having a first set of filtering characteristics and the second filter of the second type having a second set of filtering characteristics different from the first set of filtering characteristics.

2. The system of claim 1, wherein:
   measuring the one or more characteristics of the first fluid within the air duct of the BMS comprises measuring at least one of a carbon dioxide, nitrous oxide, particulate matter, or ozone levels of the first fluid;
   measuring the one or more characteristics of the second fluid after the second fluid has been filtered comprises measuring at least one of a carbon dioxide, nitrous oxide, particulate matter, or ozone levels of the second fluid;
   measuring one or more characteristics of the first fluid is performed by a first set of sensors and measuring the one or more characteristics of the second fluid after the second fluid has been filtered is performed by a second set of sensors.

3. The system of claim 1, wherein the one or more processors are further configured to:
   receive filter data from a one or more filtration sensors, the one or more filtration sensors configured to record the filter data of the plurality of filters, the filter data comprising data relating to the one or more characteristics of the fluid;
   determine when the selected filter will become inoperable; and
   select the filter of the plurality of filters based on a change in the one or more characteristics from filtering the first fluid.

4. The system of claim 1, wherein selecting the filter of the plurality of filters comprises selecting the filter of the plurality of filters in a single fluid path, wherein all of the first fluid is filtered in the single fluid path.

5. The system of claim 1, wherein selecting the filter of the plurality of filters comprises:
   selecting a path of a plurality of paths in the air duct for the fluid to flow, wherein each of the plurality of paths comprises one of the plurality of filters; and
   filtering the first fluid based on the selected path.

6. The system of claim 1, wherein the one or more processors are further configured to compare the level of the one or more characteristics measured by the one or more sensors to a predetermined threshold, the level of the one or more characteristics based on measurements from the one or more sensors.

7. The system of claim 1, wherein the one or more processors are further configured to process the first fluid based on predetermined intervals of time, wherein processing comprising filtering, heating, disinfecting, or cleaning.

8. A controller for filtering a fluid within a building management system (BMS), the controller comprising:
   a processing circuit comprising one or more processors and memory storing instructions that, when executed by the one or more processors, cause the one or more processors to perform operations comprising:
   receiving, via one or more sensors, a first set of sensor data comprising one or more characteristics of a first fluid within an air duct of the BMS;
   receiving, via the one or more sensors, a second set of sensor data comprising one or more characteristics of a second fluid after the second fluid has been filtered;
   wherein the first fluid is a pre-filtered fluid received in the air duct and the second fluid is a post-filtered supply fluid within the air duct or a post-filtered fluid within a building zone; and
   selecting a filter from at least a first filter of a first type or a second filter of a second type different than the first type based on a level of the one or more characteristics of the first fluid and the one or more characteristics of the second fluid, the first filter of the first type having a first set of filtering characteristics and the second filter of the second type having a second set of filtering characteristics different from the first set of filtering characteristics;
   generating a model of the first fluid; and
   generating predictions based on the model, wherein the model is generated based on the first set of sensor data and the second set of sensor data.

9. The controller of claim 8, wherein:
   receiving the first set of sensor data of the one or more characteristics of the first fluid within the air duct comprises measuring at least one of a carbon dioxide, nitrous oxide, particulate matter, or ozone levels of the first fluid;
   receiving the second set of sensor data of the one or more characteristics of the second fluid after the second fluid has been filtered comprises measuring at least one of a carbon dioxide, nitrous oxide, particulate matter, or ozone levels of the second fluid; and
   the first set of sensor data of the one or more characteristics of the first fluid is received by a first set of sensors and the second set of sensor data of the one or more characteristics of the second fluid is received by a second set of sensors.

10. The controller of claim 8, wherein the processing circuit is further configured to:
    receive filter data from one or more filtration sensors, the one or more filtration sensors configured to record the filter data of the plurality of filters, the filter data comprising data relating to the one or more characteristics of the fluid;
    determine when the selected filter will become inoperable; and
    select the filter of the plurality of filters based on a change in the one or more characteristics from filtering the first fluid.

11. The controller of claim 8, wherein selecting the filter of the plurality of filters comprises selecting the filter of the plurality of filters in a single fluid path, wherein all of the first fluid is filtered in the single fluid path.

12. The controller of claim 8, wherein selecting the filter of the plurality of filters comprises:
selecting a path of a plurality of paths in the air duct for the first fluid to flow, wherein each of the plurality of paths comprises one of the plurality of filters; and
filtering the first fluid based on the selected path.

13. The controller of claim 8, wherein the processing circuit is further configured to compare the level of the one or more characteristics to a predetermined threshold, the level of the one or more characteristics based on information from the first set of sensor data, the second set of sensor data, or both.

14. The controller of claim 8, wherein the processing circuit is further configured to process the first fluid based on predetermined intervals of time, wherein processing comprising filtering, heating, disinfecting, or cleaning.

15. A method for filtering a first fluid within a building management system (BMS), the method comprising:
receiving, via one or more sensors, a first set of sensor data of one or more characteristics of the first fluid within an air duct of the BMS;
receiving, via the one or more sensors, a second set of sensor data of one or more characteristics of a second fluid after the second fluid has been filtered; and
wherein the first fluid is a pre-filtered fluid received in the air duct and the second fluid is a post-filtered supply fluid within the air duct or a post-filtered fluid within a building zone; and
selecting a filter from at least a first filter of a first type or a second filter of a second type different than the first type based on a level of the one or more characteristics of the first fluid and the one or more characteristics of the second fluid, the first filter of the first type having a first set of filtering characteristics and the second filter of the second type having a second set of filtering characteristics different from the first set of filtering characteristics.

16. The method of claim 15,
wherein receiving the first set of sensor data of the one or more characteristics of the first fluid within the air duct comprises measuring at least one of a carbon dioxide, nitrous oxide, particulate matter or ozone levels of the first fluid,
receiving the second set of sensor data of the one or more characteristics of the second fluid after the second fluid has been filtered comprises measuring at least one of a carbon dioxide, nitrous oxide, particulate matter, or ozone levels of the second fluid, and
the first set of sensor data of the one or more characteristics of the first fluid is received by a first set of sensors and the second set of sensor data of the one or more characteristics of the second fluid is received by a second set of sensors.

17. The method of claim 15, wherein the method further comprises:
receiving filter data from one or more filtration sensors, the one or more filtration sensors configured to record filter data of the plurality of filters, the filter data comprising data relating to the one or more characteristics of the first fluid;
determining when the selected filter will become inoperable; and
selecting the filter of the plurality of filters based on a change in the one or more characteristics from filtering the first fluid.

18. The method of claim 15, wherein selecting the filter of the plurality of filters comprises:
selecting a path of a plurality of paths in the air duct for the first fluid to flow, wherein each of the plurality of paths comprises one of the plurality of filters; and
filtering the first fluid based on the selected path.

19. The method of claim 15, wherein the method further comprises comparing the level of the one or more characteristics of the first fluid to a predetermined threshold, the level of the one or more characteristics of the first fluid based on information from the first set of sensor data, the second set of sensor data, or both.

20. The method of claim 15, wherein the method further comprises processing the first fluid based on predetermined intervals of time, wherein processing comprising filtering, heating, disinfecting, or cleaning.

* * * * *